United States Patent
Vesely

(10) Patent No.: US 8,460,369 B2
(45) Date of Patent: Jun. 11, 2013

(54) TOOLS FOR REMOVAL AND INSTALLATION OF EXCHANGEABLE CARDIOVASCULAR VALVES

(75) Inventor: Ivan Vesely, Larkspur, CO (US)

(73) Assignee: ValveXchange Inc., Aurora, CO (US)

( * ) Notice: Subject to any disclaimer, the term of this patent is extended or adjusted under 35 U.S.C. 154(b) by 595 days.

(21) Appl. No.: 12/522,326

(22) PCT Filed: Jan. 17, 2008

(86) PCT No.: PCT/US2008/000587
§ 371 (c)(1),
(2), (4) Date: Jul. 7, 2009

(87) PCT Pub. No.: WO2008/088835
PCT Pub. Date: Jul. 24, 2008

(65) Prior Publication Data
US 2010/0004739 A1    Jan. 7, 2010

Related U.S. Application Data

(60) Provisional application No. 60/880,984, filed on Jan. 18, 2007, provisional application No. 60/899,787, filed on Feb. 6, 2007, provisional application No. 60/888,616, filed on Feb. 7, 2007.

(51) Int. Cl.
*A61F 2/24* (2006.01)

(52) U.S. Cl.
USPC ........................................ 623/2.11; 623/1.11

(58) Field of Classification Search
USPC ........ 623/1.11, 2.11, 2.18; 606/200, 205–209
See application file for complete search history.

(56) References Cited

U.S. PATENT DOCUMENTS

| | | | |
|---|---|---|---|
| 3,409,013 A | 11/1968 | Berry | 606/1 |
| 3,898,701 A | 8/1975 | LaRussa | 3/1.5 |
| 4,056,854 A * | 11/1977 | Boretos et al. | 623/2.18 |
| 4,506,394 A | 3/1985 | Bédard | 3/1.5 |
| 4,680,031 A | 7/1987 | Alonso | 128/343 |
| 4,790,843 A | 12/1988 | Carpentier et al. | 623/2 |
| 4,887,605 A | 12/1989 | Angelsen et al. | 128/660.03 |
| 4,909,789 A | 3/1990 | Taguchi et al. | 604/107 |
| 5,037,427 A | 8/1991 | Harada et al. | 606/108 |
| 5,041,130 A | 8/1991 | Cosgrove et al. | 623/2 |
| 5,071,431 A | 12/1991 | Sauter et al. | 623/2 |
| 5,087,264 A | 2/1992 | Miller et al. | 606/159 |
| 5,113,846 A | 5/1992 | Hiltebrandt et al. | 600/225 |
| 5,197,978 A | 3/1993 | Hess | 623/1.18 |
| 5,234,443 A * | 8/1993 | Phan et al. | 606/148 |
| 5,312,360 A | 5/1994 | Behl | 604/164 |

(Continued)

FOREIGN PATENT DOCUMENTS

| WO | WO 99/33414 | 7/1999 |
|---|---|---|
| WO | WO 2009/026272 | 2/2009 |

OTHER PUBLICATIONS

International Search Report for International Application No. PCT/US2008/073565, Nov. 3, 2008.

(Continued)

*Primary Examiner* — Darwin Erezo
(74) *Attorney, Agent, or Firm* — Kusner & Jaffe

(57) ABSTRACT

Tools for the removal and installation of exchangeable cardiovascular valves. The tools facilitate rapid exchange of a cardiovascular valve member mounted in the aortic position (retrograde exchange) or the mitral position (transapical exchange).

25 Claims, 26 Drawing Sheets

U.S. PATENT DOCUMENTS

| | | | |
|---|---|---|---|
| 5,336,230 A * | 8/1994 | Leichtling et al. | 606/148 |
| 5,411,552 A | 5/1995 | Andersen et al. | 623/2 |
| 5,474,563 A | 12/1995 | Myler et al. | 606/108 |
| 5,476,510 A | 12/1995 | Eberhardt et al. | 623/2.11 |
| 5,545,214 A | 8/1996 | Stevens | 623/2 |
| 5,554,185 A | 9/1996 | Block et al. | 623/2 |
| 5,571,174 A | 11/1996 | Love et al. | 623/2 |
| 5,584,803 A | 12/1996 | Stevens et al. | 604/4 |
| 5,593,424 A | 1/1997 | Northrup, III | 606/232 |
| 5,607,446 A | 3/1997 | Beehler et al. | 606/198 |
| 5,662,676 A | 9/1997 | Koninckx | 606/198 |
| 5,667,525 A * | 9/1997 | Ishibashi | 606/206 |
| 5,718,725 A | 2/1998 | Sterman et al. | 623/2 |
| 5,807,405 A | 9/1998 | Vanney et al. | 623/112 |
| 5,814,054 A * | 9/1998 | Kortenbach et al. | 606/139 |
| 5,840,081 A | 11/1998 | Andersen et al. | 623/1.11 |
| 5,843,103 A | 12/1998 | Wulfman | 606/159 |
| 5,843,181 A | 12/1998 | Jaffe et al. | 623/2 |
| 5,855,601 A | 1/1999 | Bessler et al. | 623/2 |
| 5,910,144 A * | 6/1999 | Hayashi | 606/108 |
| 5,910,170 A | 6/1999 | Reimink et al. | 623/2 |
| 5,957,949 A | 9/1999 | Leonhardt et al. | 606/194 |
| 6,004,328 A | 12/1999 | Solar | 606/108 |
| 6,071,263 A | 6/2000 | Kirkman | 604/104 |
| 6,106,550 A | 8/2000 | Magovern et al. | 623/2.38 |
| 6,156,055 A * | 12/2000 | Ravenscroft | 606/206 |
| 6,168,614 B1 | 1/2001 | Andersen et al. | 623/1 |
| 6,168,616 B1 | 1/2001 | Brown | 623/1.11 |
| 6,187,016 B1 | 2/2001 | Hedges et al. | 606/108 |
| 6,197,054 B1 | 3/2001 | Hamblin, Jr. et al. | 623/2.38 |
| 6,217,585 B1 | 4/2001 | Houser et al. | 606/108 |
| 6,312,465 B1 | 11/2001 | Griffin et al. | 623/2.38 |
| 6,383,205 B1 | 5/2002 | Samson et al. | 606/200 |
| 6,508,827 B1 * | 1/2003 | Manhes | 606/205 |
| 6,530,952 B2 | 3/2003 | Vesely | 623/2.18 |
| 6,579,305 B1 | 6/2003 | Lashinski | 623/1.11 |
| 6,629,534 B1 | 10/2003 | St. Goar et al. | 128/898 |
| 6,769,434 B2 * | 8/2004 | Liddicoat et al. | 128/898 |
| 6,821,297 B2 * | 11/2004 | Snyders | 623/2.18 |
| 6,893,459 B1 | 5/2005 | Macoviak | 623/2.11 |
| 7,041,132 B2 * | 5/2006 | Quijano et al. | 623/2.11 |
| 7,063,707 B2 | 6/2006 | Bose et al. | 606/127 |
| 7,201,761 B2 * | 4/2007 | Woolfson et al. | 606/170 |
| 7,323,003 B2 * | 1/2008 | Lowe | 606/200 |
| 7,329,279 B2 * | 2/2008 | Haug et al. | 623/2.11 |
| 7,381,219 B2 * | 6/2008 | Salahieh et al. | 623/2.11 |
| 7,544,206 B2 * | 6/2009 | Cohn | 623/2.11 |
| 7,815,676 B2 | 10/2010 | Greenberg | 623/2.11 |
| 7,824,442 B2 * | 11/2010 | Salahieh et al. | 623/2.11 |
| 7,824,443 B2 * | 11/2010 | Salahieh et al. | 623/2.11 |
| 7,959,666 B2 * | 6/2011 | Salahieh et al. | 623/1.26 |
| 7,959,672 B2 * | 6/2011 | Salahieh et al. | 623/2.17 |
| 7,993,362 B2 * | 8/2011 | Lowe et al. | 606/200 |
| 8,025,668 B2 * | 9/2011 | McCartney | 606/106 |
| 2001/0002445 A1 * | 5/2001 | Vesely | 623/2.11 |
| 2002/0128702 A1 | 9/2002 | Menz et al. | 623/1.12 |
| 2002/0173811 A1 | 11/2002 | Tu et al. | 606/159 |
| 2004/0039442 A1 | 2/2004 | St. Goar et al. | 623/2.36 |
| 2004/0147939 A1 | 7/2004 | Rabkin et al. | 606/108 |
| 2005/0137692 A1 | 6/2005 | Haug et al. | 623/2.11 |
| 2005/0165479 A1 * | 7/2005 | Drews et al. | 623/2.38 |
| 2005/0203614 A1 | 9/2005 | Forster et al. | 623/2.11 |
| 2005/0216079 A1 | 9/2005 | MaCoviak | 623/2.38 |
| 2005/0228495 A1 | 10/2005 | Macoviak | 623/2.18 |
| 2006/0287717 A1 | 12/2006 | Rowe et al. | 623/2.11 |
| 2007/0027535 A1 | 2/2007 | Purdy et al. | 623/2.18 |
| 2007/0088431 A1 | 4/2007 | Bourang et al. | 623/2.11 |
| 2007/0260305 A1 | 11/2007 | Drews et al. | 623/2.11 |
| 2008/0004696 A1 * | 1/2008 | Vesely | 623/2.1 |
| 2008/0033545 A1 | 2/2008 | Bergin et al. | 623/2.11 |
| 2008/0065011 A1 | 3/2008 | Marchand et al. | 604/103.02 |
| 2008/0071367 A1 | 3/2008 | Bergin et al. | 623/2.11 |
| 2008/0228254 A1 * | 9/2008 | Ryan | 623/1.2 |
| 2010/0004739 A1 * | 1/2010 | Vesely | 623/2.11 |
| 2011/0257735 A1 * | 10/2011 | Salahieh et al. | 623/2.11 |
| 2012/0016469 A1 * | 1/2012 | Salahieh et al. | 623/2.11 |
| 2012/0041549 A1 * | 2/2012 | Salahieh et al. | 623/2.11 |
| 2012/0046740 A1 * | 2/2012 | Paul et al. | 623/2.11 |
| 2012/0053683 A1 * | 3/2012 | Salahieh et al. | 623/2.11 |
| 2012/0078354 A1 * | 3/2012 | Cohn | 623/2.11 |

OTHER PUBLICATIONS

International Search Report for International Application No. PCT/US2009/56633, Nov. 13, 2009.

* cited by examiner

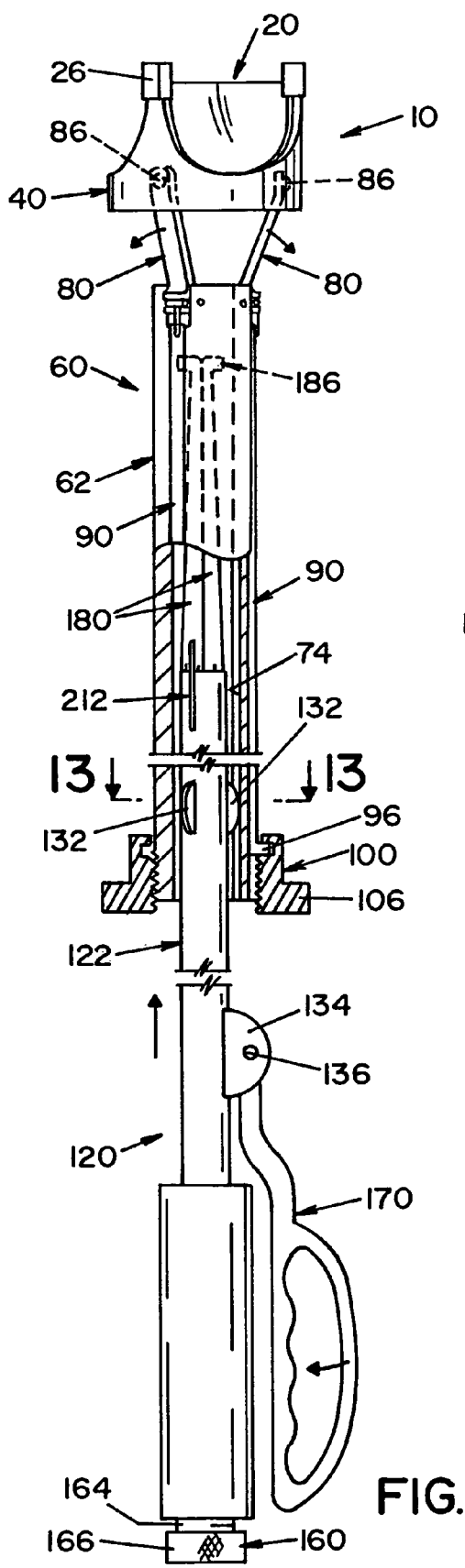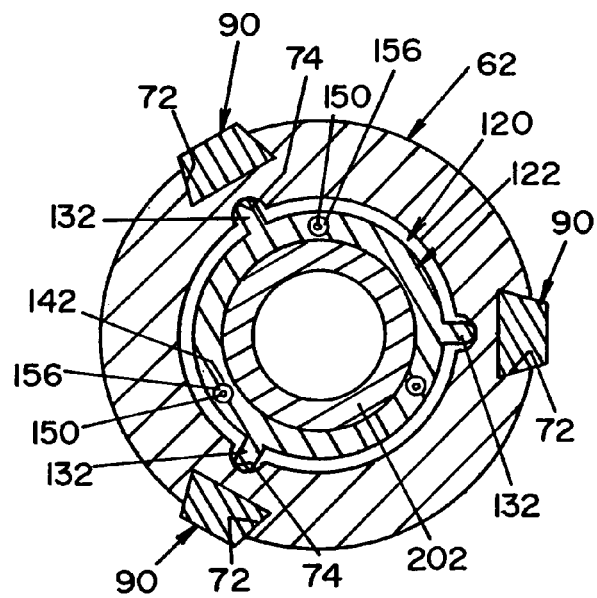
FIG. 12
FIG. 13

TOOLS FOR REMOVAL AND INSTALLATION OF EXCHANGEABLE CARDIOVASCULAR VALVES

RELATED APPLICATIONS

This application claims the benefit of U.S. Provisional Application Nos. 60/880,984 (filed Jan. 18, 2007); 60/899,787 (filed Feb. 6, 2007); and 60/888,616 (filed Feb. 7, 2007), all of which are fully incorporated herein by reference.

FIELD OF INVENTION

The present invention relates generally to the field of cardiovascular valves, and more particularly to tools that facilitates the removal and installation of exchangeable cardiovascular valves.

BACKGROUND OF THE INVENTION

The demographics of patients suffering valvular disease are broad and the treatment modalities for each are complex. Historically, patients younger than 65 years of age have been prescribed mechanical heart valves, while older patients have been prescribed bioprosthetic heart valves that are comprised of biological tissue mounted on a plastic or metallic supporting structure. However, the role of the patient in choosing a particular valve type is changing. In this regard, younger patients that are active now frequently opt for bioprosthetic valves, since such patients are unwilling to deal with the lifestyle changes that are required by mechanical valves and the associated chronic anticoagulation therapy. These patients would much rather have repeat surgeries to replace a worn-out bioprosthetic valve, than deal with the lifestyle changes required by mechanical valves.

In view of the need for replacement of bioprosthetic heart valves, a cardiovascular valve assembly has been developed comprising a valve member, including a leaflet component, and a docking station (also referred to herein as a "base member"). The docking station is permanently installed, and the valve member is detachably engaged with the docking station to allow exchange of the valve member. Accordingly, this two-piece valve assembly enables a valve member having a worn-out leaflet component to be exchanged without requiring open-heart surgery and long periods on cardiopulmonary bypass.

The present invention is directed to tools that facilitate the removal and installation of an exchangeable valve member.

SUMMARY OF THE INVENTION

In accordance with one aspect of the present invention, there is provided a holding tool for facilitating the exchange of a valve member of a valve assembly that includes a valve member detachably coupled to a base member, the holding tool comprising: a body; a plurality of fingers mounted to the body and moveable between a collapsed position and an expanded position, said fingers engageable with the base member in the expanded position; and an actuator for actuating movement of the fingers between the collapsed and expanded positions.

In accordance with another aspect of the present invention, there is provided a tool for facilitating the exchange of a valve member of a valve assembly that includes a valve member detachably coupled to a base member, the tool comprising: a body; a plurality of arms mounted to the body and moveable between a collapsed position and an expanded position, said arms engageable with the valve member in the expanded position; and a first actuator for actuating movement of the arms between the collapsed and expanded positions.

In accordance with still another aspect of the present invention, there is provided a locating tool for facilitating the exchange of a valve member of a valve assembly that includes a valve member detachably coupled to a base member, the locating tool comprising: a body, defining an opening dimensioned to receive a holding tool engageable with said base member; a plurality of snare loops, each snare loop comprised of a snare wire; a plurality of moveable sleeves, each sleeve enclosing a portion of a snare wire; first control means for moving the snare loops between a retracted position and a loosened position; and second control means for moving the sleeves between a retracted position and an extended position.

In accordance with yet another aspect of the present invention, there is provided a holding tool for facilitating the exchange of a valve member of a valve assembly that includes a valve member detachably coupled to a base member, the holding tool comprising: a tubular body, an inner rod moveable within the tubular body; an articulating joint member connected to the tubular body and the inner rod, said articulating joint member moveable between a collapsed position and an expanded position, wherein movement of the inner rod relative to the tubular body moves the articulating joint member between the collapsed and expanded positions.

An advantage of the present invention is the provision of a tool for facilitating the removal of an exchangeable cardiovascular valve member from a docking station, wherein the exchangeable cardiovascular valve member is disengaged from a docking station.

Another advantage of the present invention is the provision of a tool for facilitating the installation of an exchangeable cardiovascular valve member, wherein the exchangeable valve member is engaged with a docking station.

Still another advantage of the present invention is the provision of tools for facilitating the rapid removal and installation of an exchangeable valve member, thereby minimizing the amount of time on cardiopulmonary bypass.

Yet another advantage of the present invention is the provision of tools that facilitate rapid exchange of a valve member mounted in the aortic or mitral positions.

These and other advantages will become apparent from the following description of embodiments of the present invention taken together with the accompanying drawings and the appended claims.

BRIEF DESCRIPTION OF THE DRAWINGS

The invention may take physical form in certain parts and arrangement of parts, an embodiment of which will be described in detail in the specification and illustrated in the accompanying drawings which form a part hereof, and wherein:

FIG. 12 shows the removal tool of FIG. 8 partially inserted into the holding tool of FIG. 3, the holding tool in engagement with a base member of a valve assembly;

FIG. 13 is a cross-sectional view of the removal tool located within the holding tool, taken along lines 13-13 of FIG. 12;

DETAILED DESCRIPTION OF THE INVENTION

Figure 1:
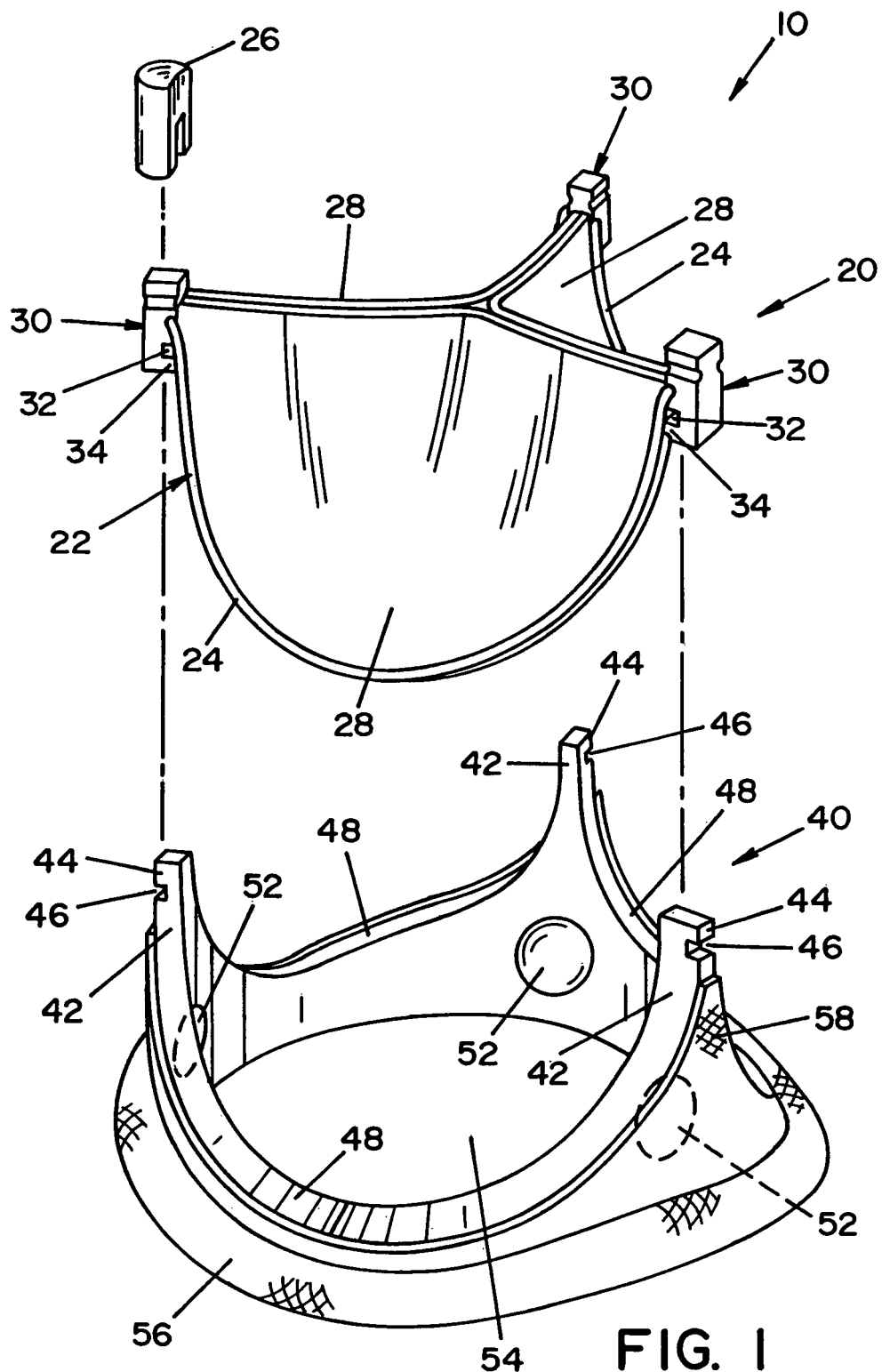
FIG. 1 is an exploded view of a cardiovascular valve assembly adapted for use with the tools of the present invention, the valve assembly including an exchangeable valve member and a docking station.

Referring now to the drawings wherein the showings are for the purpose of illustrating embodiments of the present invention only and not for the purposes of limiting same, FIG. 1 illustrates a cardiovascular valve assembly 10 adapted for use in connection with the tools of the present invention. Valve assembly 10 is comprised of a docking station or base member 40 and a valve member 20 detachably coupled to base member 40. In the illustrated embodiment, valve member 20 is a bioprosthetic valve. However, it is contemplated that valve member 20 may also take the form of a mechanical valve.

Base member 40 is generally comprised of a plurality of mounting portions 42 and a plurality of arcuate sections 48 located between mounting portions 42. Each mounting portion 42 includes an outward extending tab 44 and a recess 46. Mounting portions 42 and arcuate sections 48 define a generally cylindrical recess 54. A plurality of holes, recesses or depressions 52 are formed on the inner surface of base member 40. In the illustrated embodiment, depressions 52 have a hemispherical shape. However, it is contemplated that depressions 52 may have other shapes, including but not limited to, a raised or recessed tab or hook.

A sewing cuff or ring 56 is attached to the outer surface of base member 40 for permanent attachment of base member 40 to the tissue of the heart. Sewing ring 56 may also include a sleeve portion 58 to provide further coverage of the outer surface of base member 40.

Valve member 20 is generally comprised of a frame 22 including a plurality of wireform sections 24 and coupling elements 30, and one or more valve leaflets 28. Coupling element 30 includes an inward facing recess 32 and an inward extending tab 34. A fabric cover 26 may be placed over each coupling element. Coupling elements 30 allow valve member 20 to be coupled and uncoupled from base member 40, as will be described below. Each wireform section 24 has a generally arcuate shape, and extends between coupling elements 30. Wireform sections 24 have an arcuate shape that matches the profile of arcuate sections 48 of base member 40, thereby forming a seal.

Wireform sections 24 are preferably made of a medical grade metal wire with suitable elasticity to facilitate the engagement and disengagement of coupling element 30 and mounting portion 42. Suitable materials include, but are not limited to, Elgiloy, nitinol, stainless steel, platinum, gold, titanium, other biocompatible metals, and combinations thereof. It should be understood that a preferred material for wireform sections 24 has an elasticity such that the material returns to its original shape after being deformed.

Leaflets 28 are supported by frame 22. Leaflets 28 may be made of suitable materials, including, but not limited to, bovine pericardium, equine pericardium, ovine pericardium, porcine aortic valve tissue, small intestinal submucosa (SIS), various biodegradable substrates for tissue engineered valves, and various relatively inert polymers, such as polyurethane. Wireform sections 24 are covered with Dacron or other suitable medical grade covering, and leaflets 28 sewn to that covering. Alternatively, leaflets 28 may be attached directly to wireform sections 24 by appropriate means, such as sutures, clips, staples or other fastening devices.

Coupling elements 30 allow valve member 20 to be coupled and uncoupled from base member 40. As indicated above, recess 32 of coupling element 30 is dimensioned to receive tab 44 of mounting portion 42. Similarly, recess 46 of mounting portion 42 is dimensioned to receive tab 34 of coupling element 30. Valve member 20 is coupled and uncoupled from base member 40 through engagement and disengagement of coupling element 30 and mounting portion 42.

Figure 2:
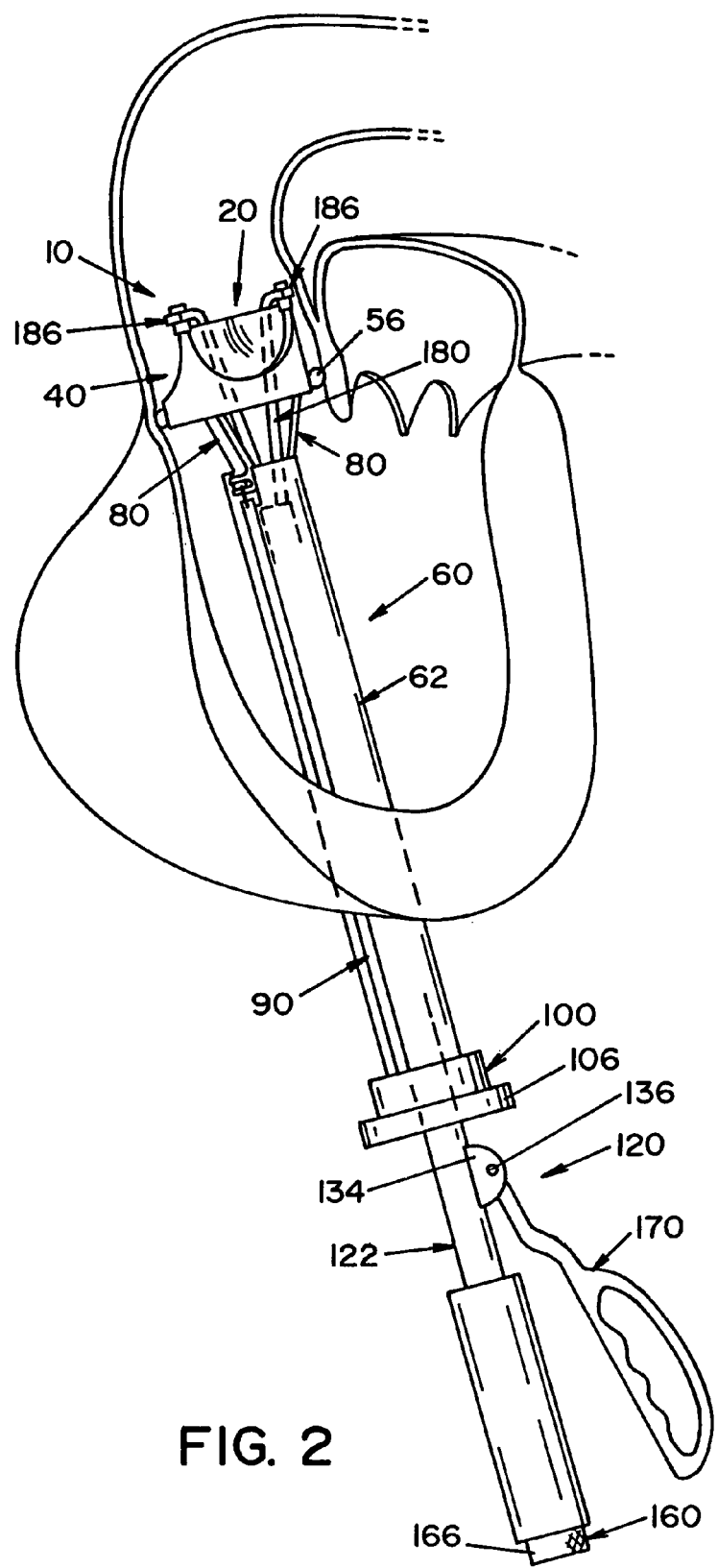
FIG. 2 is a schematic view overlay illustrating a valve holding tool inserted through the apex of a heart, with a valve removal tool inserted through the holding tool, wherein the holding tool is engaged with a base member of a valve assembly and the valve removal tool is engaged with a valve member of the valve assembly, the valve assembly shown in the aortic position.

Referring now to FIG. 2, there is shown a schematic view of a heart with first embodiments of a holding tool 60 and a valve removal tool 120 located therein to detach and remove valve member 20 from base member 40. More specifically, holding tool 60 and removal tool 120 are shown inserted through the apex of the heart (i.e., "transapical" approach). A "purse-string" suture (not shown) is located around the outer surface of holding tool 60. Holding tool 60 is engaged with base member 40 of valve assembly 10, while removal tool 120 is engaged with valve member 20 of valve assembly 10. A detailed description of the components and operation of holding tool 60 and removal tool 120 is provided below.

Referring now to FIGS. 3-7, holding tool 60 will be described in detail. Holding tool 60 is generally comprised of a tubular body 62, fingers 80, elongated rods 90 and an actuator 100.

Tubular body 62 is a generally hollow tube, similar to a conventional "trocar" that defines a generally cylindrical opening. A series of rubberized, flexible valves (not shown) are located within body 62 to allow surgical tools and other devices (as will be described below) to be passed through the inner chamber of body 62, in and out off the interior of the heart, without allowing pressurized blood or gasses to escape. Pivoting fingers 80 move between a collapsed position and an expanded position wherein fingers 80 engage with base member 40, as will be described in detail below.

Figure 3:
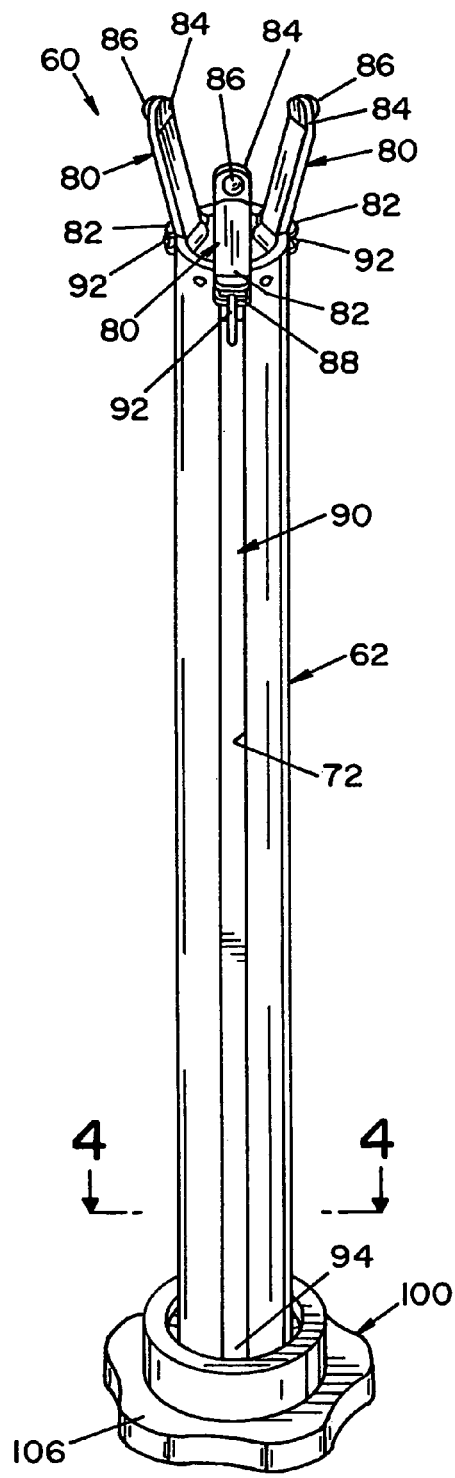
FIG. 3 is a perspective view of the holding tool according to an embodiment of the present invention, the holding tool used to hold a base member and locate a valve removal tool.
Figure 4:
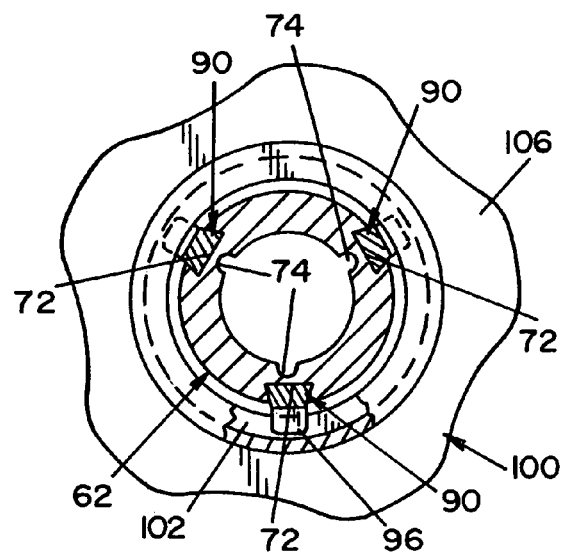
FIG. 4 is a cross-sectional view of the holding tool, taken along lines 4-4 of FIG. 3.

As best seen in FIGS. 3 and 4, a plurality of grooves or channels 72 extend longitudinally along the outer surface of tubular body 62. Channels 72 are dimensioned to receive elongated rods 90. Rods 90 preferably mate with channels 72 in a "dove tail" configuration to maintain rods 90 within channels 72.

Figure 6:
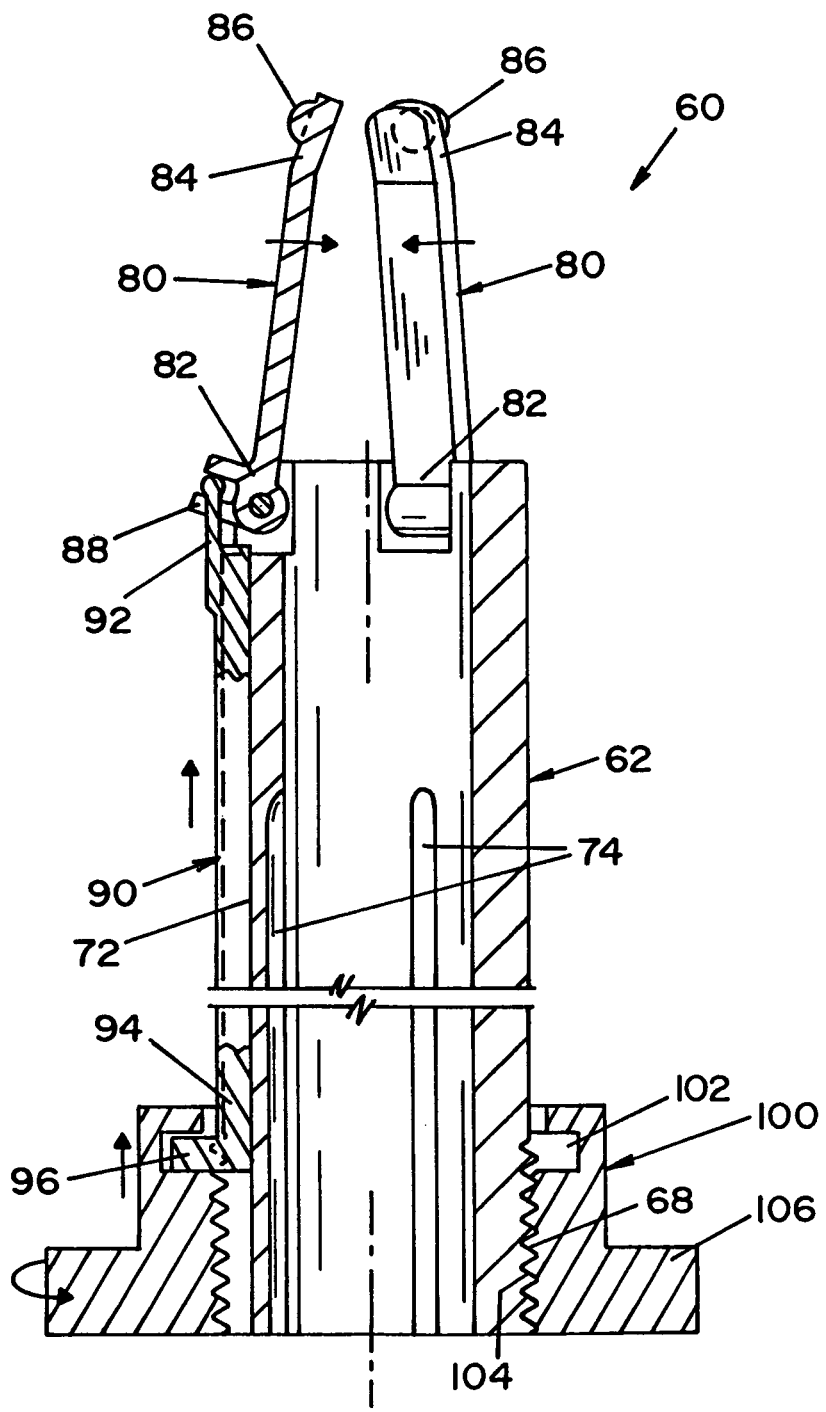
FIG. 6 is a cross-sectional view of the holding tool shown in FIG. 3.
Figure 7:
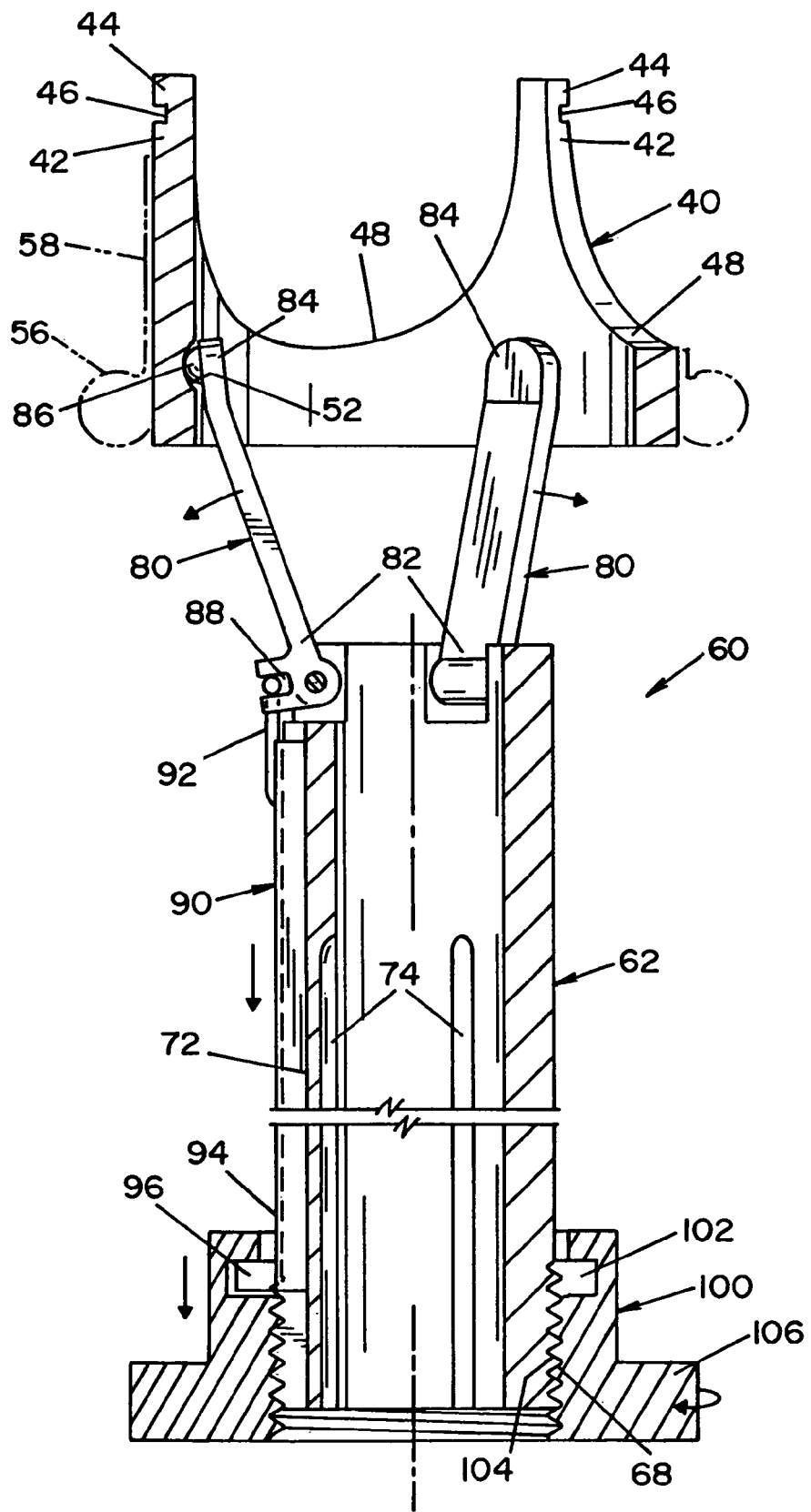
FIG. 7 is a cross-sectional view of the holding tool shown in FIG. 3, as engaged with a base member of a valve assembly.

A plurality of inner grooves 74 extend longitudinally along the inner surface of tubular body 62, as best seen in FIGS. 4 and 6-7. Grooves 74 facilitate the locating of removal tool 120 relative to valve member 20, as will be explained below.

Figure 5:
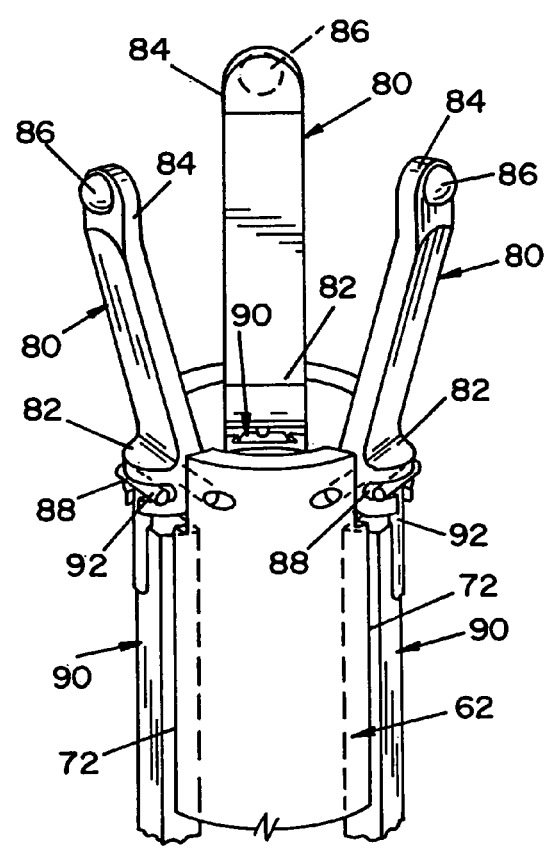
FIG. 5 is an enlarged view of one end of the holding tool, showing moveable fingers for engaging the base member of a valve assembly.

At one end of tubular body 62, threads 68 are formed on the outer surface thereof, and mate with threads of actuator 100 which is described in detail below. At the other end of tubular body 62, a plurality of fingers 80 are pivotally attached thereto, as best seen in FIGS. 5-7. Each finger 80 has a first end 82 pivotally connected with tubular body 62, and a second end 84 having an outward facing protuberance 86 formed therein (see FIGS. 3 and 5-6). In the illustrated embodiment, second end 84 is angled inward. Fingers 80 also have a T-shaped slot 88 at first end 82 to connect to rod 90, as best seen in FIG. 5. Protuberance 86 is dimensioned to be received by depression 52 in base member 40, as will be explained below. In the embodiment shown, protuberance 86 has a hemispherical shape. However, it is contemplated that protuberance 86 may have an alternative geometry and configuration, including a needle that extends outward from an appropriately shaped pad to facilitate locating protuberance 86 within depression 52.

Each rod 90 has a first end 92 that is generally T-shaped (best seen in FIG. 5), and a second end 94 that includes an outward extending tab 96 (best seen in FIGS. 6 and 7). T-shaped end 92 is dimensioned to be received by T-shaped slot 88 of finger 80, as best seen in FIG. 5.

As best seen in FIGS. 6 and 7, actuator 100 is generally ring-shaped, and has an annular inner groove 102, inner threads 104 and an annular flange 106. Annular inner groove 102 is dimensioned to capture tab 96 of rod 90. Inner threads 104 mate with outer threads 68 of tubular body 62. Flange 106 provides a gripping surface to facilitate rotation of actuator 100.

Rotation of actuator 100 causes axial movement of rods 90, which in turn, causes fingers 80 to pivot between an inward collapsed position (FIG. 6) and an outward expanded position (FIG. 7). In the expanded position of fingers 80, protuberances 86 are located within depression 52 formed in base member 40, thereby securely engaging holding tool 60 with base member 40.

It is contemplated that alternative interengagement means may be substituted for protuberances 86 and depressions 52, and that the interengagement means may be reversed (e.g., protuberances 86 are formed on base member 40 and depressions 52 are formed on fingers 80). It is further contemplated that rods 90 may be interconnected with actuator 100 and fingers 80 by alternative means. It should also be appreciated that alternative interengagement means may also be used in the other embodiments discussed below.

Removal tool 120 will now be described with reference to FIGS. 8-11. Removal tool 120 is generally comprised of a hollow cylindrical body 122, a plurality of arms 180 having respective gripping elements 186, a cylindrical inner sleeve 202, a plurality of links 212 for connecting arms 180 to inner sleeve 202, an arms actuator 170 for controlling movement of arms 180, and a gripping elements actuator 160 for controlling movement of gripping elements 186.

Figures 8, 9:
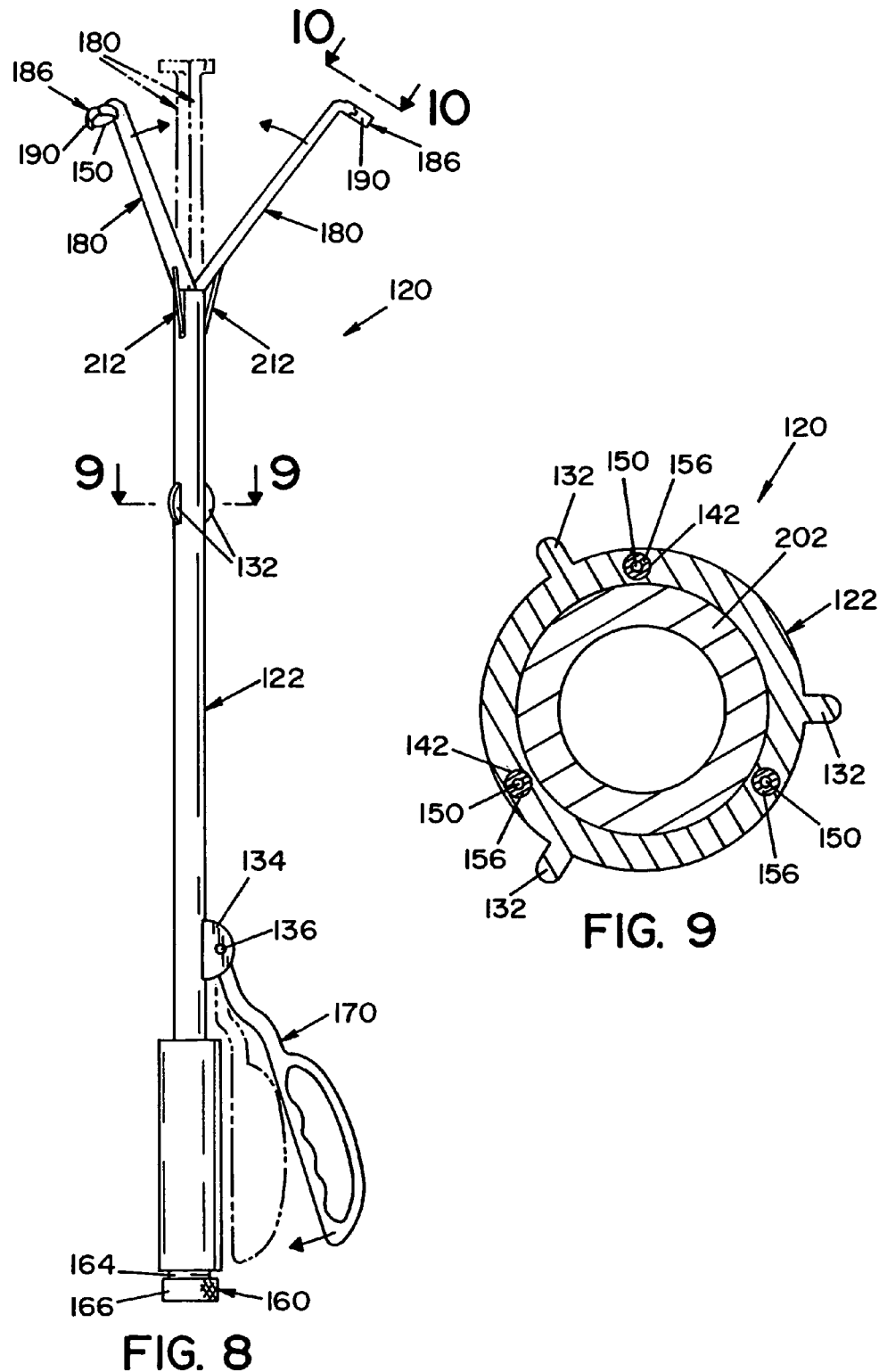
FIG. 8 is a side elevation view of a valve removal tool according to an embodiment of the present invention, the removal tool used for removing a valve member from a base member of a valve assembly.
FIG. 9 is a cross-sectional view of the valve removal tool, taken along lines 9-9 of FIG. 8.
Figure 11:
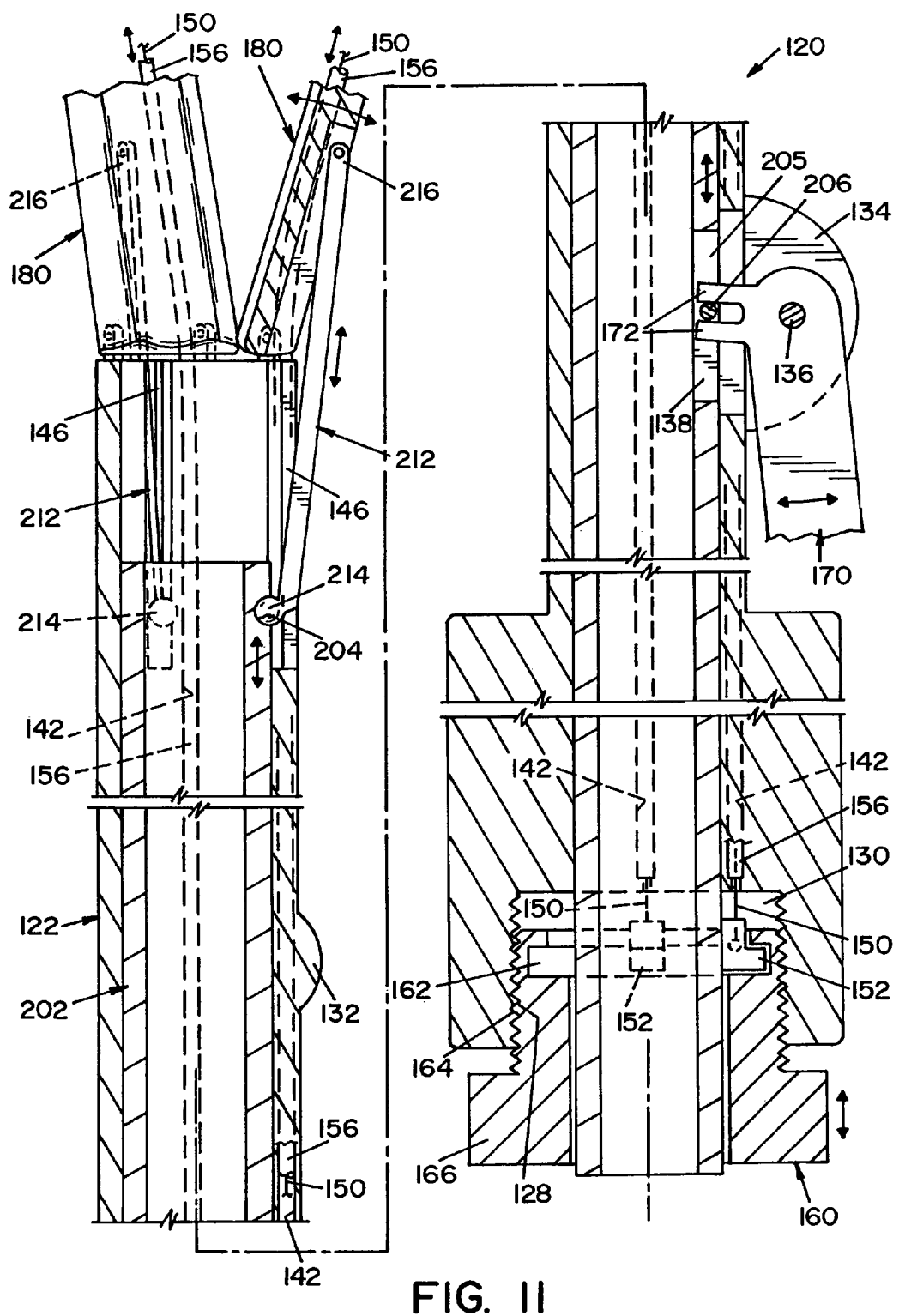
FIG. 11 is a cross-sectional view the removal tool shown in FIG. 8.
Figure 14:
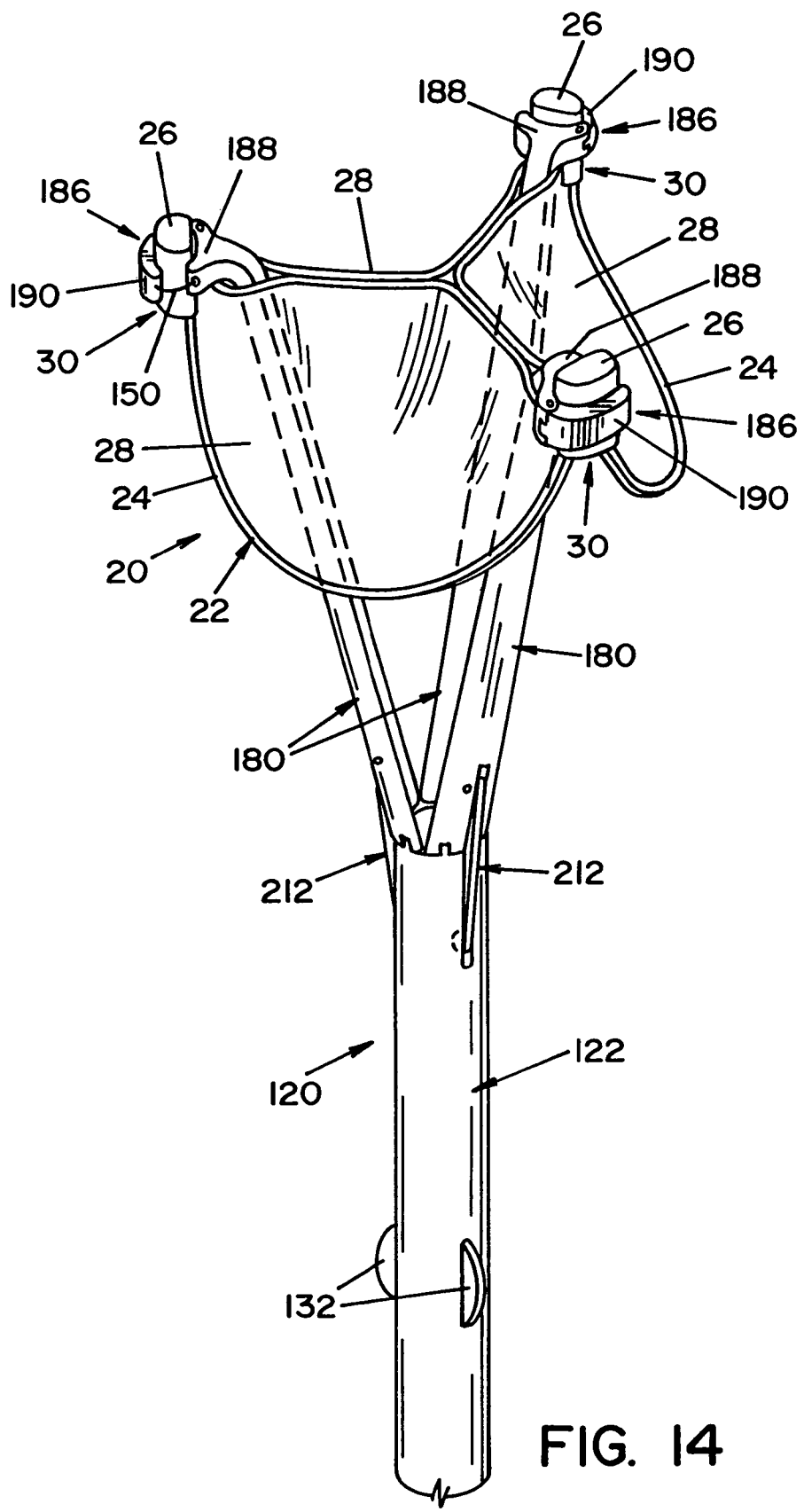
FIG. 14 is a perspective view of the removal tool grasping a valve member, the arms of the removal tool in an expanded position.
Figure 15:
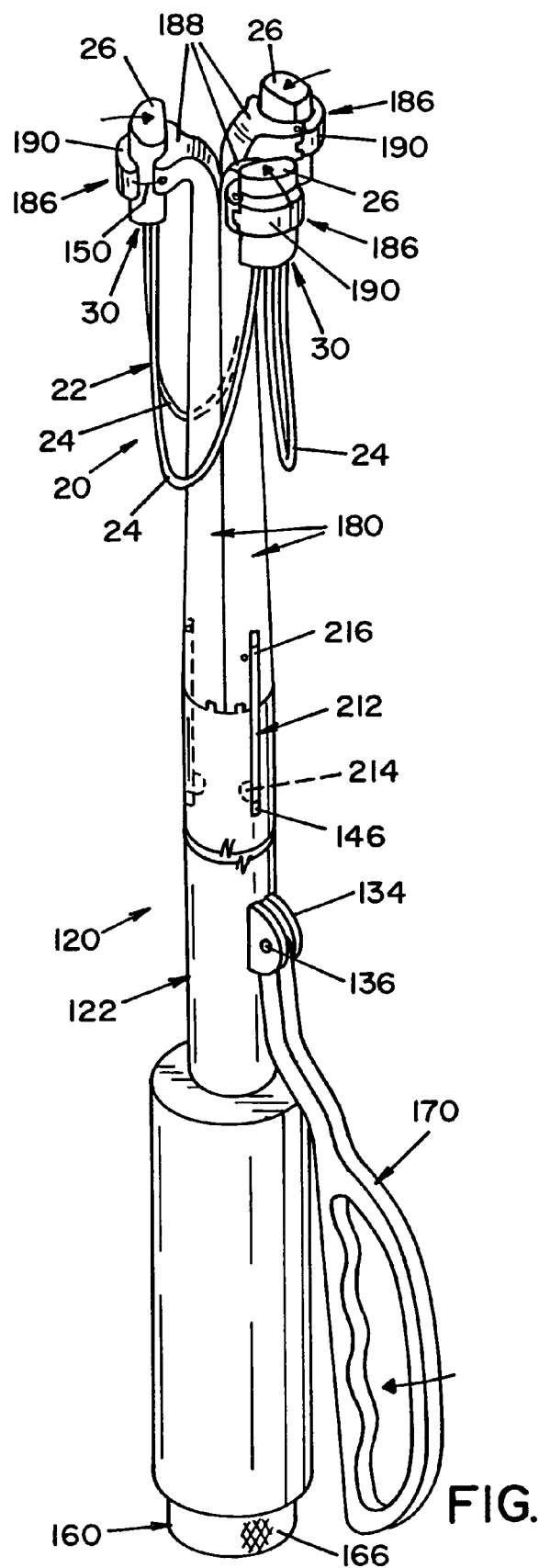
FIG. 15 is a perspective view of the removal tool grasping a valve member, the arms of the removal tool in a collapsed position, thereby collapsing the valve member.

Inner sleeve 202 is located inside cylindrical body 122, as best seen in FIGS. 9 and 11. Axial movement of inner sleeve 202 within cylindrical body 122 results in movement of arms 180 between a collapsed position and an expanded position, as shown in FIG. 8. Inner sleeve 202 is connected with arms 180 via links 212, best seen in FIG. 11. The first end 214 of link 212 has a ball hinge that is dimensioned to be received by a generally spherical cavity 204 formed in inner sleeve 202. The second end 216 of link 212 is pivotally connected to arm 180. Link 212 extends through a slot 146 in cylindrical body 122 to connect with inner sleeve 202. Inner sleeve 202 also includes a slot 205 and a pin 206. Pin 206 extends across slot 205, as shown in FIG. 11 to operatively connect inner sleeve 202 with actuator 170.

Cylindrical body 122 includes a cylindrical recess 130 located at one end thereof, as best seen in FIG. 11. Inner threads 128 are formed in cylindrical recess 130. Cylindrical recess 130 is dimensioned to receive actuator 160 that is used to control the movement of gripping elements 186. Actuator 160 is a generally tubular screw having an annular inner groove 162, outer threads 164 and an annular flange 166. Outer threads 164 mate with inner threads 128 of cylindrical body 122. Flange 166 provides a gripping surface to facilitate rotation of actuator 160.

A bracket member 134 extends outward from the outer surface of body 122, as seen in FIGS. 8 and 11. Bracket member 134 supports arms actuator 170 that is pivotally attached to bracket member 134 by a pivot pin 136. Actuator 170 includes fingers 172 that extend through a slot 138 formed in body 122, as seen in FIG. 11. Fingers 172 capture pin 206 of inner sleeve 202. Rotation of actuator 170 causes axial movement of inner sleeve 202, thereby moving arms 180 between the collapsed and expanded position. In the illustrated embodiment, actuator 170 is a "scissor-like" handle.

Figure 10:
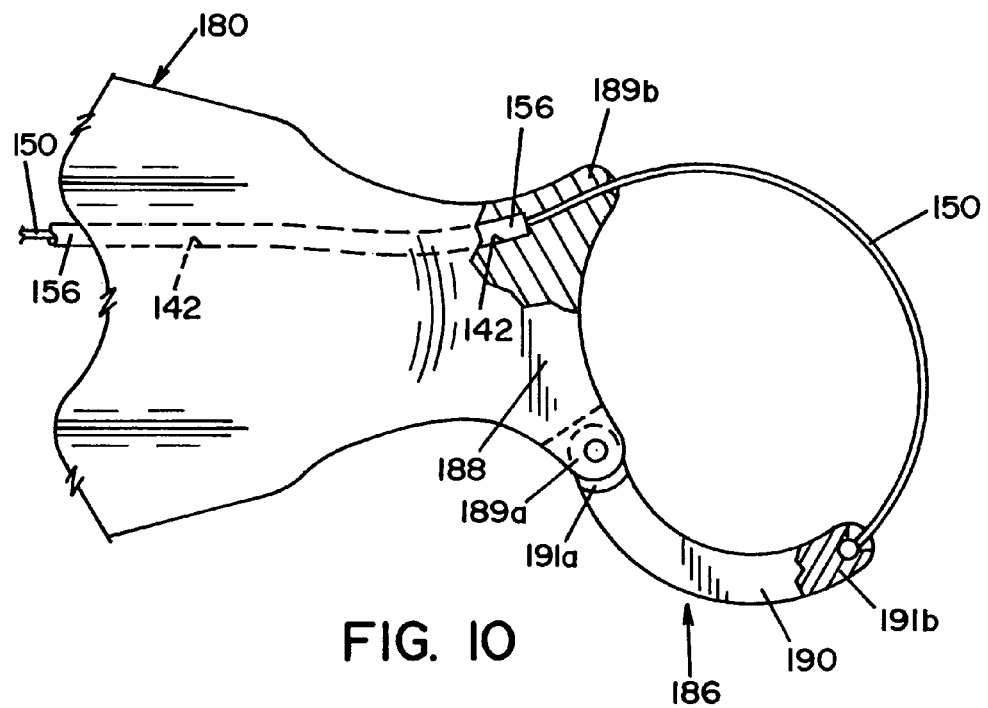
FIG. 10 is an enlarged view partially in section of a gripping element of the removal tool taken along lines 10-10 of FIG. 8, the gripping element shown in an open position.

Referring to FIGS. 9-11, a plurality of inner channels 142 extend through the walls of body 122 and arms 180. A cable 150, moveable within a sheath 156, is located in each inner channel 142. L-shaped tab 152 is located at one end of cable 150, as shown in FIG. 11. Tab 152 is captured within annular inner groove 162 of actuator 160. Cable 150 operatively connects actuator 160 with gripping elements 186.

Figure 10A:
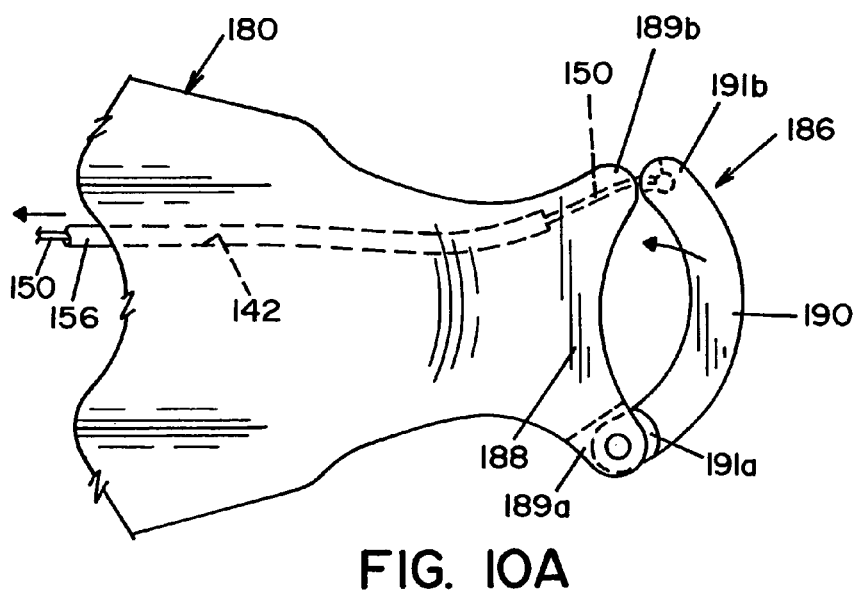
FIG. 10A is an enlarged view of a gripping element of the removal tool of FIG. 8, the gripping element shown in a closed position.

As mentioned above, each arm 180 includes a gripping element 186 (as shown in FIG. 8) that acts as an articulating pincer or jaw. Gripping element 186 includes a Y-shaped portion 188 and a C-shaped portion 190, as shown in detail in FIGS. 10 and 10A. End 191a of C-shaped portion 190 is pivotally attached to end 189a of Y-shaped portion 188. End 191b of C-shaped portion 190 is attached to cable 150 extending from end 189b of Y-shaped portion 188. Cable 150 is used to move end 191b of C-shaped portion 190 towards and away from end 189b of Y-shaped portion 188, thereby moving gripping element 186 between an open position (FIG. 10) and a closed position (FIG. 10A)

When actuator 160 is screwed inward into recess 130 of body 122, cable 150 moves gripping element 186 to the open position (FIG. 10). Likewise, when actuator 160 is screwed outward from recess 130 of body 122, cable 150 moves gripping element to the closed position (FIG. 10A).

A plurality of locating members 132 extend outward from the outer surface of body 122, as best seen in FIG. 8. Inner grooves 74 of holding tool 60 are dimensioned to receive locating members 132. Locating members 132 and grooves 74 facilitate the alignment of removal tool 120 relative to valve member 20 (see FIGS. 12 and 13), as will be described below. It should be appreciated that locating members 132 may take various forms, including plastic or spring metal.

It is contemplated that removal tool 120, as disclosed herein or with minor modifications, may also function as a valve installation tool. In this regard, a valve member 20 may be inserted into a heart and engaged with base member 40 by reversing the steps of the operation discussed above for removal of valve member 20 from base member 40.

It should be appreciated that levers, pull-wires, and pulleys may also be used as a means for moving fingers 80 of holding tool 60 and arms 180 of removal tool 120. It should be further appreciated that arms 180 of removal tool 120 may have articulating joints (not shown) to facilitate movement of gripping elements 186 to a desired position.

Operation of holding tool 60 and removal tool 120 will now be described with reference to a "transapical approach" to valve exchange (see FIG. 2). A transapical approach to valve exchange can be summarized as follows:

(i) exposure of the apex of the heart and the establishment of a "trocar" port by insertion of holding tool 60;

(ii) engagement of fingers 80 of holding tool 60 with base member 40 of valve assembly 10;

(iii) insertion of removal tool 120 and grasping of coupling elements 30 of valve member 20;

(iv) dilation, unseating and collapsing of frame 22 of valve member 20;

(v) removal of valve member 20 through holding tool 60;

(vi) insertion of a new valve member 20 through holding tool 60, using removal tool 120 as an installation tool (or a dedicated valve insertion tool);

(vii) expansion and seating of new valve member 20 in base member 40;

(viii) collapsing and removal of removal tool 120; and (ix) removing holding tool 60 from the heart and closure of the apical incision to the heart.

Operation of holding tool 60 and removal tool 120 using a "transapical approach" to valve exchange will now be described in further detail with reference to FIGS. 6-7 and 12-15. Holding tool 60 inserted into a heart with fingers 80 in the collapsed position (FIG. 6). Holding tool 60 is then located relative to base member 40 such that protuberances 86 of fingers 80 are received by depressions 52 of base member 40. In this respect, fingers 80 are moved to the expanded position (FIG. 7) by rotation of actuator 100. When protuberances 86 are located within depressions 52, holding tool 60 is rigidly engaged with base member 40, thereby allowing considerable force to be applied to valve member 20, without imposing any force on the heart itself.

After fingers 80 are securely engaged with base member 40, as shown in FIG. 12, removal tool 120 is inserted through holding tool 60 by first aligning locating members 132 of removal tool 120 with respective inner grooves 74 of holding tool 60 (see FIG. 13). Arms 180 of removal tool 120 are in the collapsed position when inserting removal tool 120 through holding tool 60. It should be appreciated that holding tool 60 establishes a frame of reference and angular orientation that is transferred to removal tool 120, thereby allowing gripping elements 186 of arms 180 to be easily aligned with coupling elements 30 of valve member 20. In this regard, once locating members 132 of removal tool 120 are inserted into inner grooves 74 of holding tool 60, movement of removal tool 120 is generally limited to the axial direction. This angular alignment has the benefit of pre-aligning the gripping elements 186 of arms 180 with the coupling elements 30 of exchangeable valve member 20, thereby facilitating grasping of coupling elements 30 with gripping elements 186. The shaft of removal tool 120 preferably has markings on the outer surface of cylindrical body 120 to determine the depth of insertion of removal tool 120 and facilitate locating gripping elements 186 proximate to coupling elements 30. In this manner, removal tool 120 can be easily and accurately inserted to a prescribed depth, and coupling elements 30 can be grasped by gripping elements 186 without the need for direct visualization.

Once gripping elements 186 are aligned with coupling elements 30, arms 180 are moved to the expanded position by use of actuator 170 and gripping elements 186 are moved from the open position to the closed position by use of actuator 160. Movement of gripping elements 186 from the open position to the closed position allows gripping elements 186 to capture coupling elements 30, and disengage valve member 20 from base member 40 (see FIG. 14). Arms 180 are then moved to the collapsed position by use of actuator 170, thereby collapsing frame 22 of valve member 20 (see FIG. 15). Thereafter, removal tool 120 is withdrawn from holding tool 60. It should be noted that leaflets 28 are omitted from FIG. 15 for clarity.

Figure 16:
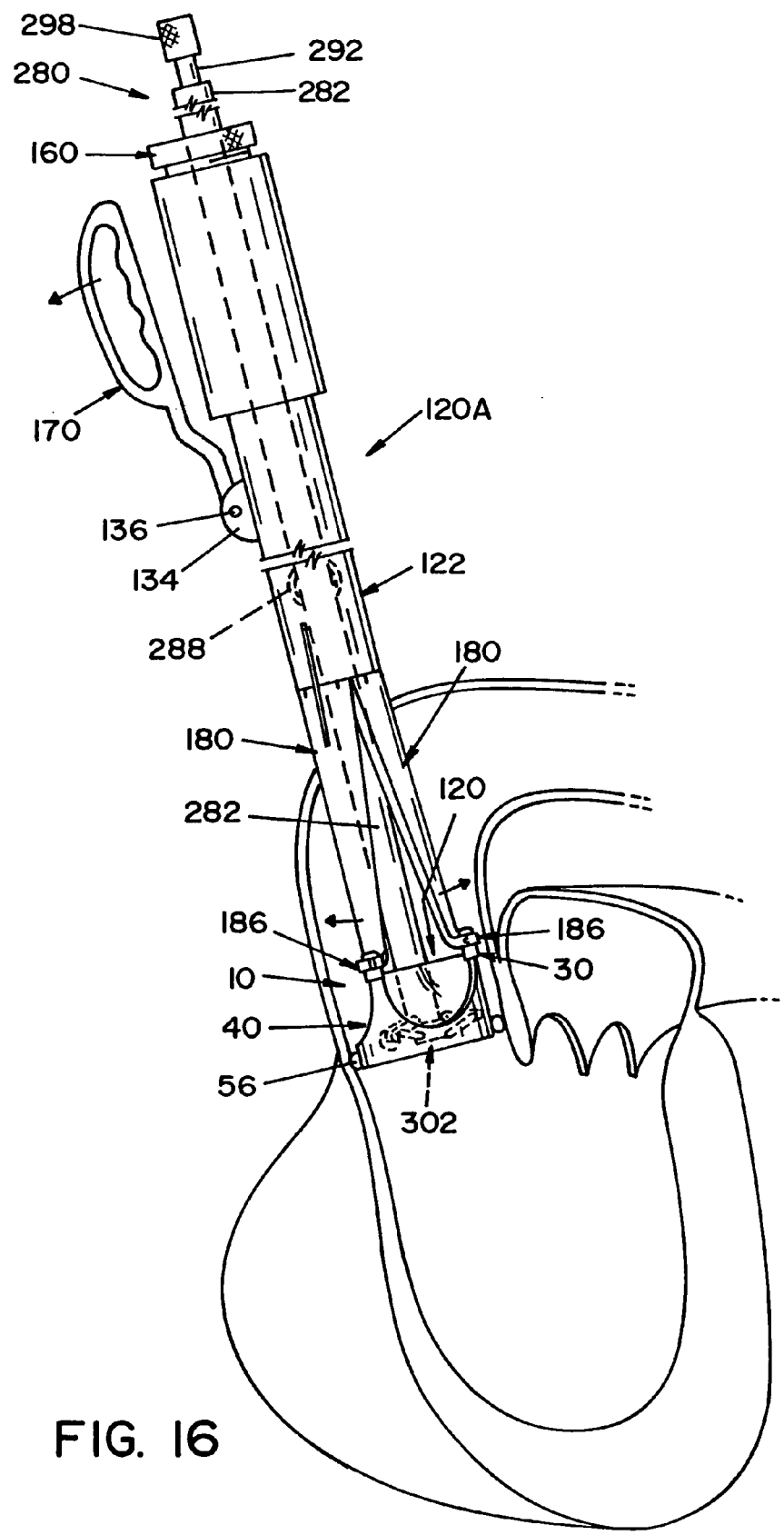
FIG. 16 is a schematic view of a valve holding tool and a valve removal tool, according to another embodiment of the present invention, wherein the valve holding tool and valve removal tool are passed through an incision in the ascending aorta during a valve exchange process.
Figure 17:
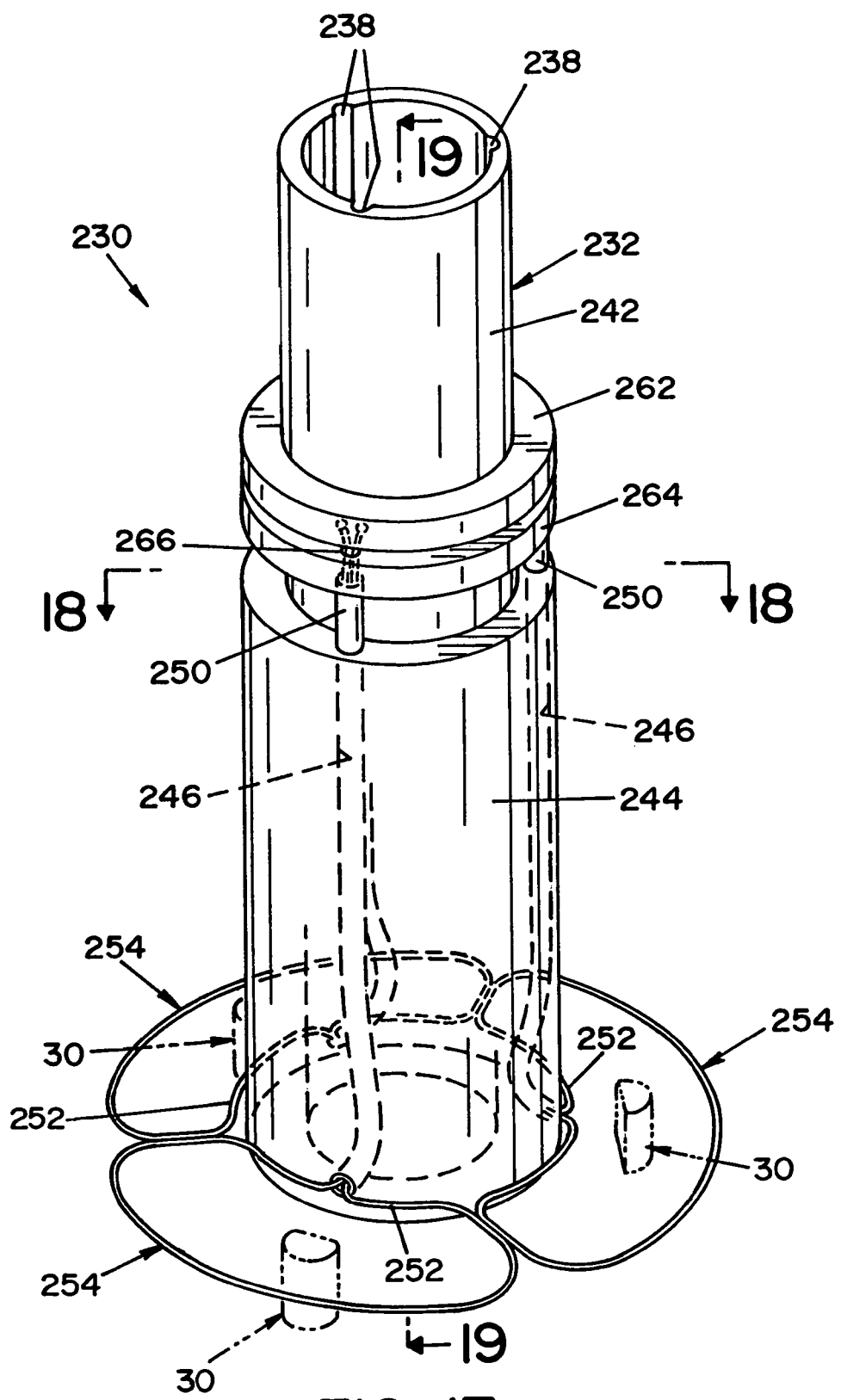
FIG. 17 is a perspective view of a locating tool according to an embodiment of the present invention, the locating tool including snare wires engageable with a valve assembly to locate a holding tool relative to the base member of the valve assembly.
Figure 18:
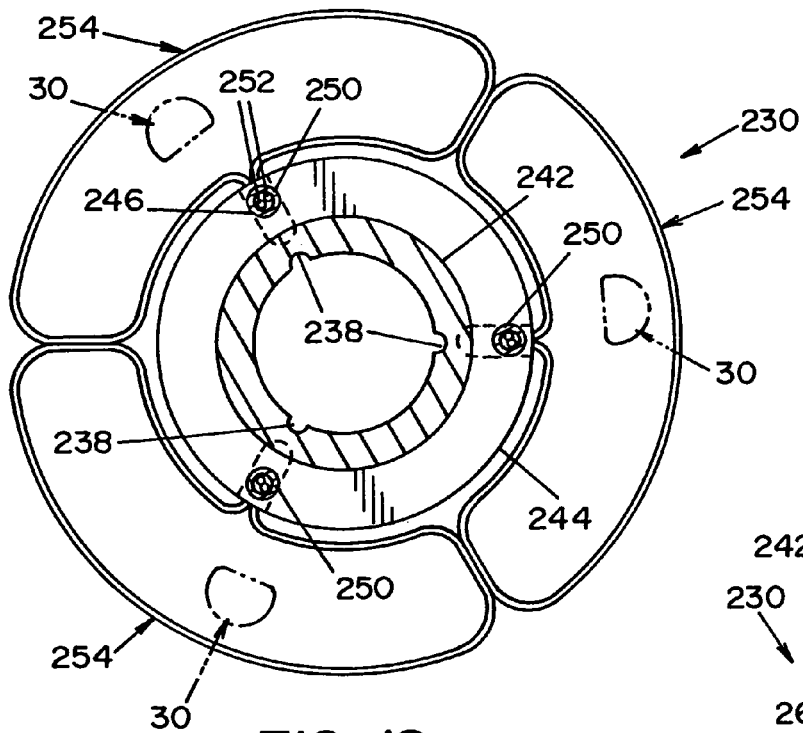
FIG. 18 is a cross-sectional view of the locating tool, taken along lines 18-18 of FIG. 17.
Figure 19:
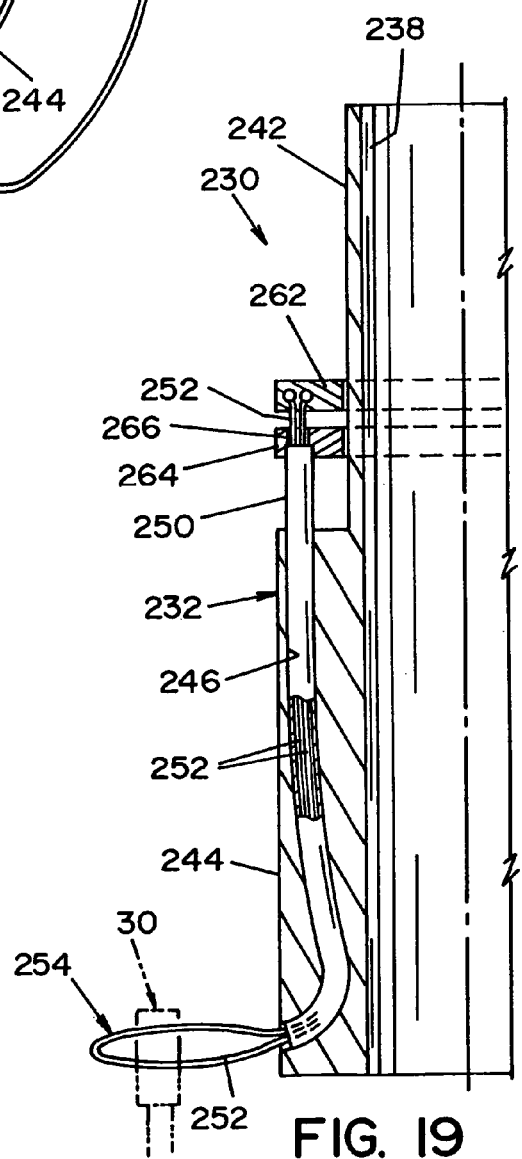
FIG. 19 is a partial cross-sectional view of the locating tool, taken along lines 19-19 of FIG. 17.

Referring now to FIG. 16, there is shown a schematic view of a valve holding tool 280 according to another embodiment and a valve removal tool 120A according to another embodiment. Valve holding tool 280 and valve removal tool 120A are shown passing through an incision in the ascending aorta during a valve exchange process. Holding tool 280 is engaged with base member 40 of valve assembly 10 and gripping elements 186 of removal tool 120A grasp coupling elements of valve member 20.

According to an embodiment of the present invention, a locating tool 230, shown in FIGS. 17-22, facilitates locating valve holding tool 280 relative to valve member 40. In the illustrated embodiment, locating tool 230 is generally comprised of a tubular body 232 defining a generally cylindrical opening. Body 232 includes a first section 242 and a second section 244, wherein second section 244 has a larger outer diameter than first section 242. A plurality of grooves 238 extend longitudinally along the inner surface of body 232. A plurality of lumens or channels 246 extend longitudinally through the wall of second section 244. Locating tool 230 also includes a first moveable ring 262 and a second moveable ring 264 that surround the outer surface of first section 242. Second moveable ring 264 is connected with a plurality of sleeves 250 that respectively extend through the plurality of channels 246 in second section 244. First movable ring 262 is connected with a plurality of snare wires 252 that extend through holes 266, formed in second moveable ring 264, and through sleeves 250 that extend through channels 246. Snare wires 252 are pre-formed into a plurality of snare loops 254 at one end of locating tool 230. In the illustrated embodiment, adjacent snare loops 254 are weakly joined together using an adhesive (e.g., a glue including silicon rubber) in order to maintain a loop shape. Snare loops 254 are dimensioned to capture coupling elements 30 of valve member 20, as will be discussed below.

Figure 20:
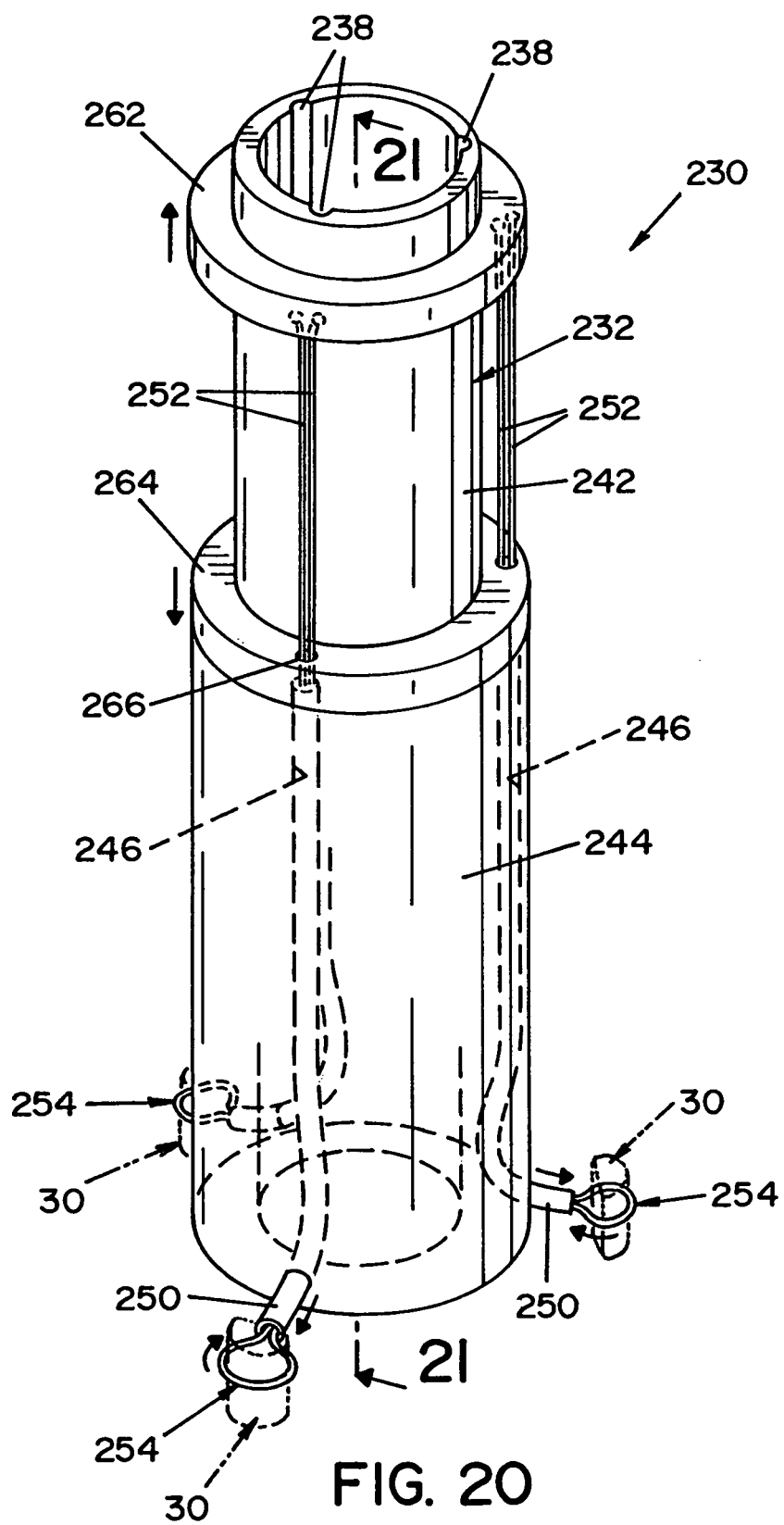
FIG. 20 is a perspective view of the locating tool of FIG. 17 showing moveable sleeves in an extended position for tightening the snare wires.
Figure 21:
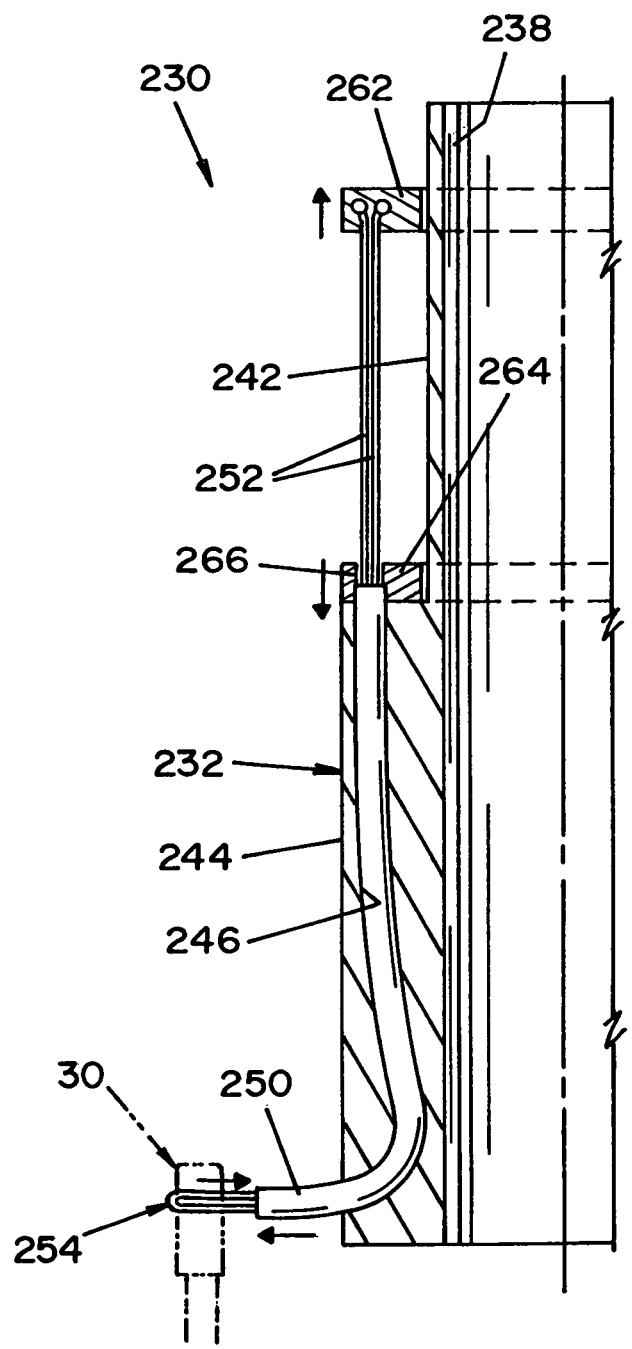
FIG. 21 is a cross-sectional view of the locating tool, taken along lines 21-21 of FIG. 20.

With reference to FIGS. 20 and 21, first and second moveable rings 262, 264 are slidable in the longitudinal direction to control movement of snare wire 252 and sleeve 250. In this respect, first moveable ring 262 is moveable away from second section 244 to retract snare loops 254, thereby separating adjacent snare loops 254 from each other and tightening snare loops 254 around coupling elements 30. Second moveable ring 264 is movable toward second section 244 to extend a portion of sleeves 250 outside channels 246, thereby further securing snare loops 254 to coupling elements 30. In the illustrated embodiment, all sleeves 250 are simultaneously extended by second moveable ring 264.

Figure 23:
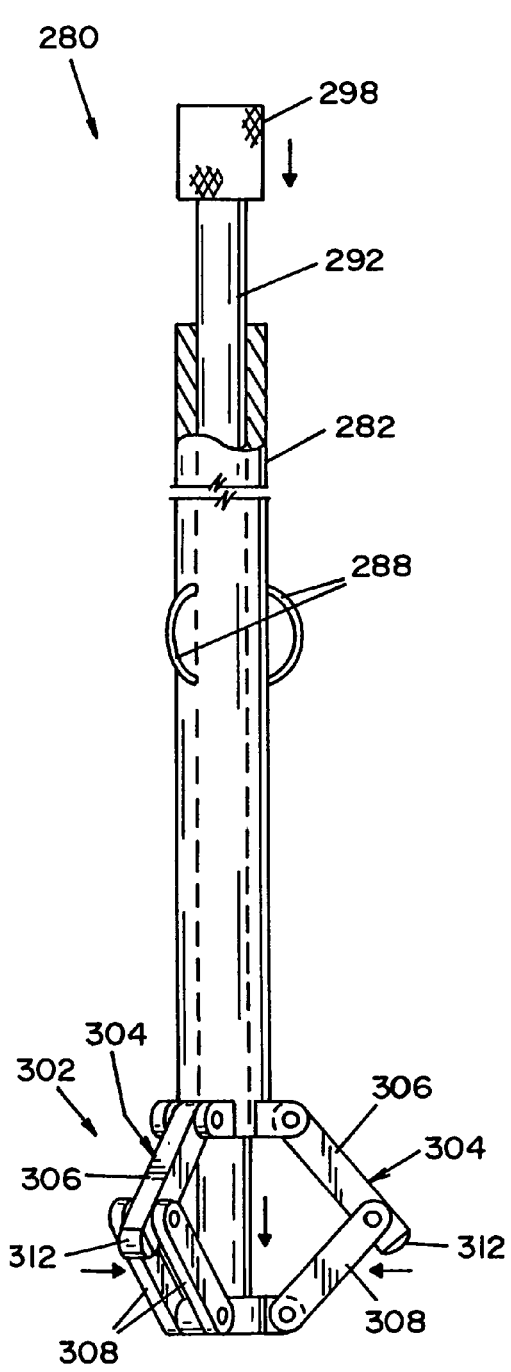
FIG. 23 is an elevational view, partially in section, of a valve holding tool according to another embodiment of the present invention, wherein an articulating joint member is shown in a partially expanded position.

Holding tool 280 will now be described with reference to FIGS. 23-25. Holding tool 280 is generally comprised of a tubular body 282, an inner rod 292 and an articulating joint member 302. Tubular body 282 defines a cylindrical recess dimensioned to receive rod 292. A plurality of locating means 288 extend outward from the outer surface of tubular body 282. In the illustrated embodiment, locating means 288 take the form of spring metal loops. The function of locating means 288 is to locate removal tool 120A relative to valve member 20, as will be described below.

One end of rod 292 is connected with tubular body 282 by articulating joint member 302, while the other end of rod 292 has a handle portion 298 for longitudinally moving rod 292 relative to tubular body 282. Articulating joint member 302 is comprised of a plurality of articulating legs 304. Each articulating leg 304 includes first and second leg sections 306 and 308 that are pivotally connected to each other. First leg section 306 is pivotally connected at one end with tubular body 282 and second leg section 308 is pivotally connected at one end with rod 292. A protuberance 312 is located at the end of first leg section 306 pivotally connected with second leg section 308. Protuberance 312 is dimensioned to be received by depression 52 of base member 40.

Figure 24:
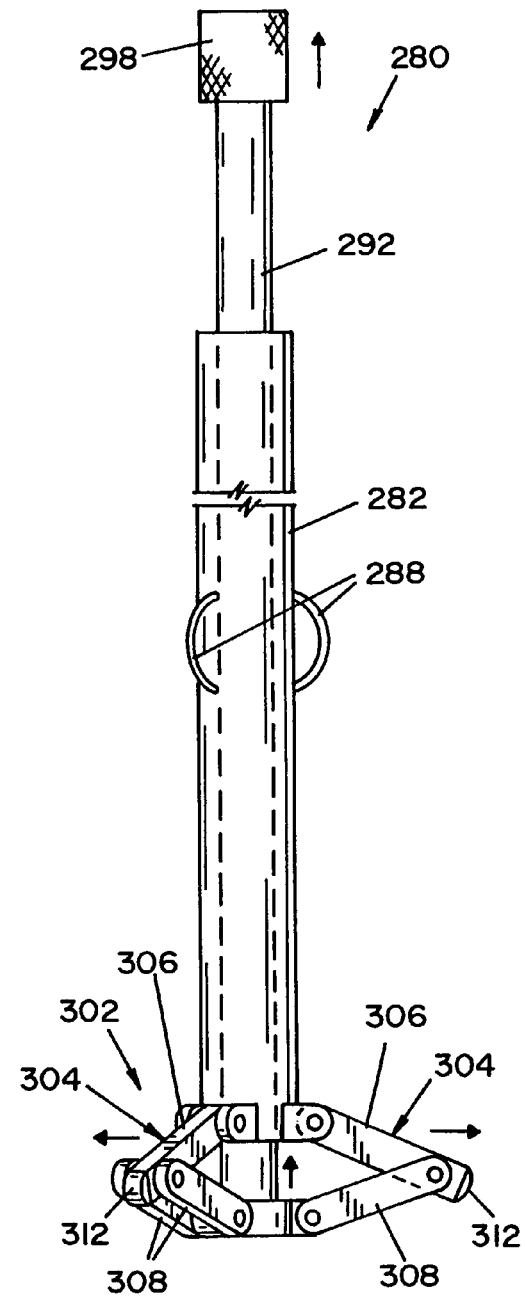
FIG. 24 is an elevational view of the holding tool of FIG. 23, wherein the articulating joint member is shown in a fully expanded position.
Figure 25:
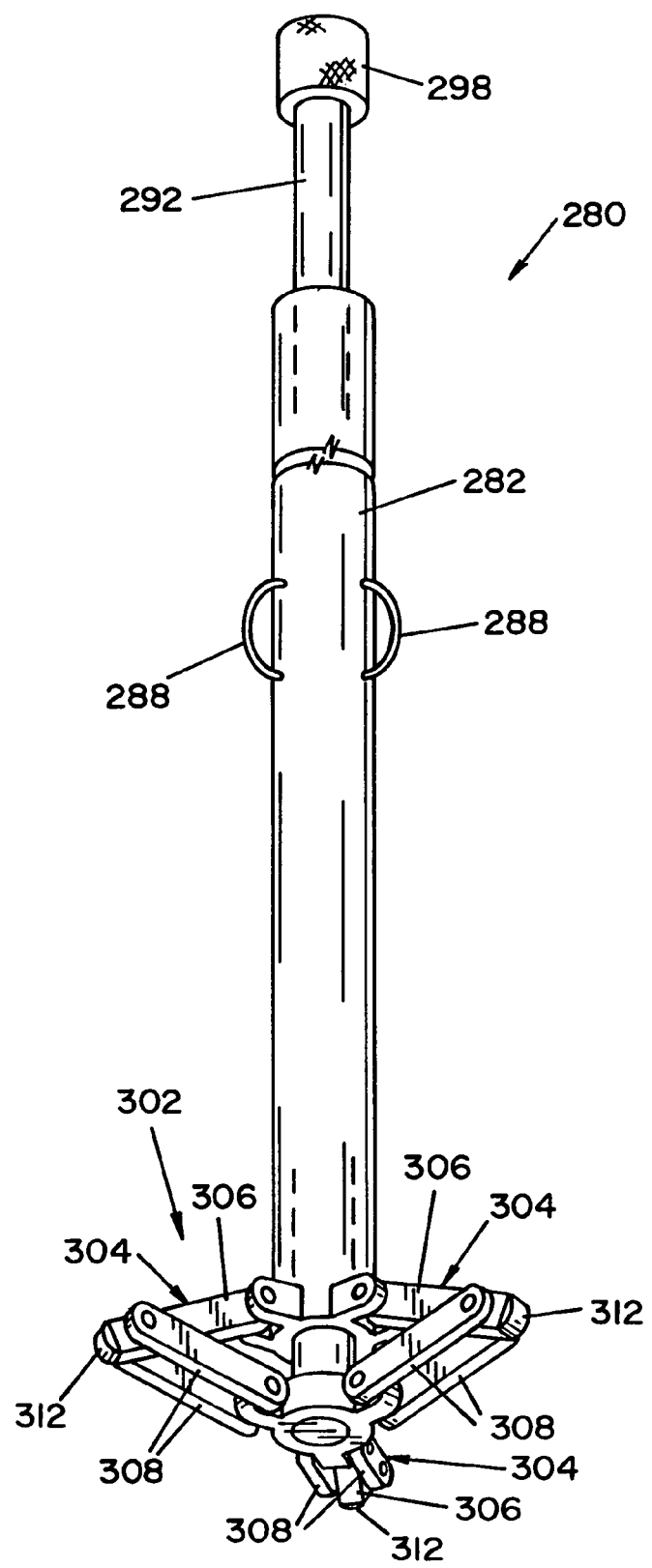
FIG. 25 is another perspective view of the valve holding tool of FIG. 23, wherein the articulating joint member is shown in the fully expanded position.

As rod 292 is moved relative to tubular body 282, articulating joint member 302 moves between a collapsed position (FIG. 23) and an expanded position (FIGS. 24 and 25). In the expanded position, protuberances 312 are received by depressions 52 of base member 40 in order to engage holding tool 280 therewith.

It is contemplated that articulating joint member 302 of holding tool 280 and base member 40 of valve assembly 10 may have alternative configurations. In one alternative configuration holes are substituted for depressions 52 in base member 40, and articulating legs 304 of articulating joint member 302 are configured such that protuberances 312 are maintained in alignment at a fixed angle (e.g., perpendicular) relative to holes in base member 40, as legs 304 are articulated. In this alternative embodiment, holes in base member 40 are preferably diamond-shaped holes and protuberances 312 are pin-shaped. Diamond-shaped holes allow some angular misalignment during insertion and facilitate angular alignment as the user pushes or pulls on holding tool 280.

Figure 28:
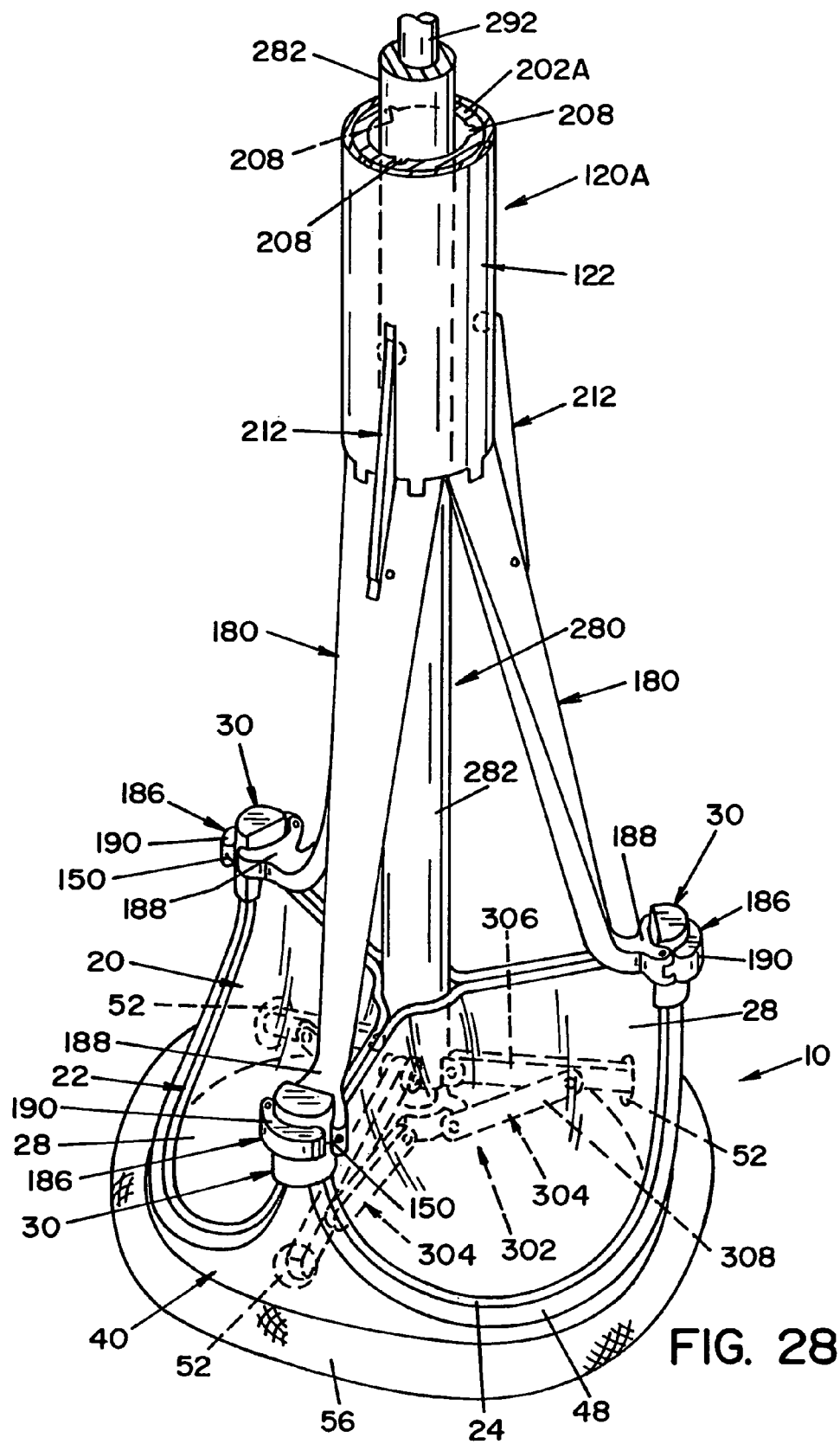
FIG. 28 shows an alternative embodiment of the valve removal tool fit over the holding tool as shown in FIG. 27, wherein the valve removal tool is in engagement with the valve member.
Figure 29:
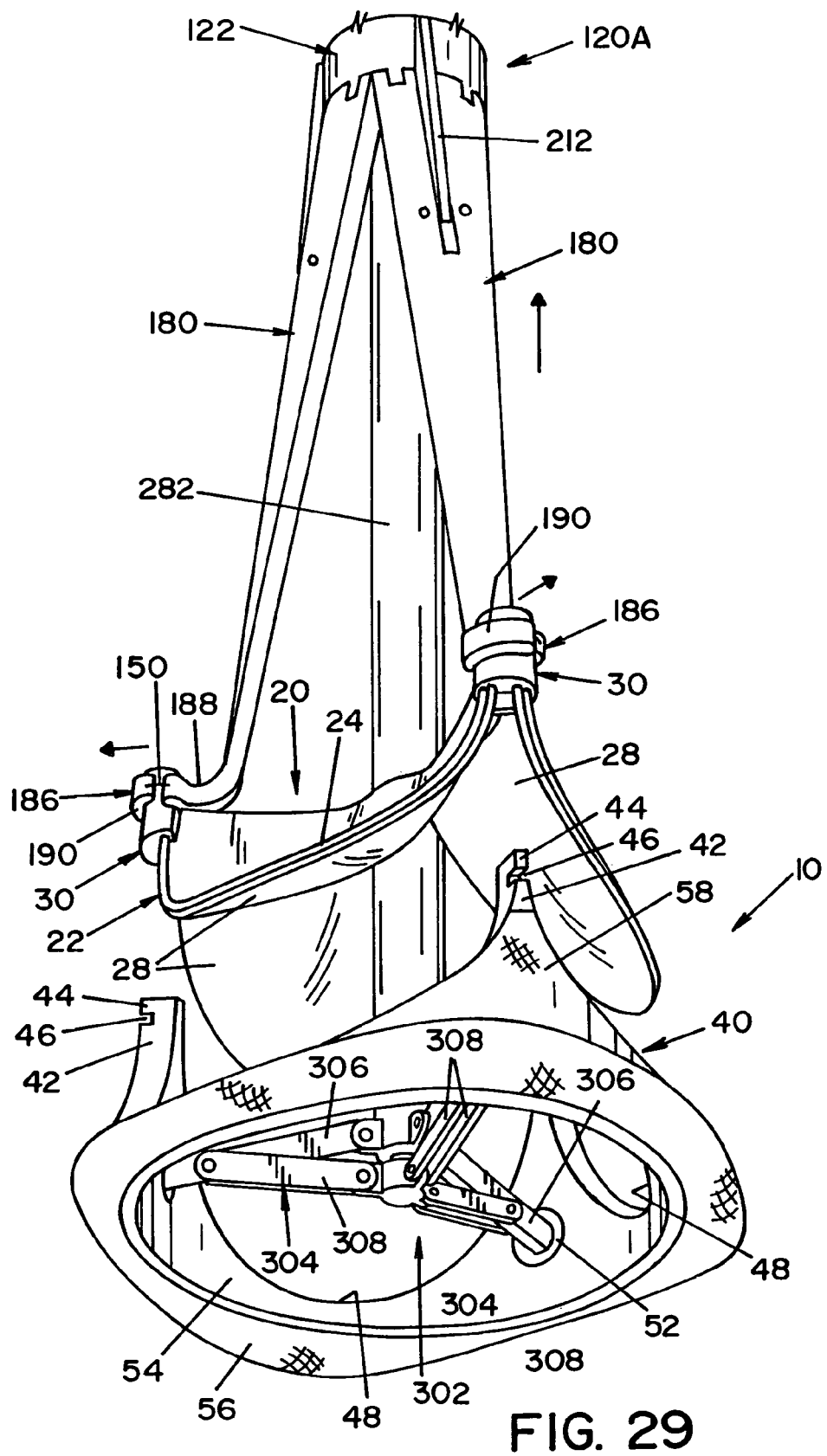
FIG. 29 shows the valve removal tool of FIG. 28, wherein the valve member is detached from the base member.

Removal tool 120A, best seen in FIGS. 28 and 29, is substantially the same as removal tool 120 described above. However, removal tool 120A has a hollow inner sleeve 202A that defines an opening dimensioned to receive holding tool 280. Grooves 208 extend longitudinally along the inner surface of inner sleeve 202A, and are dimensioned to receive locating means 288 extending from the outer surface of tubular body 282. Components of removal tool 120A similar to components of removal tool 120 bear the same reference numbers.

FIG. 16 illustrates a "retrograde" approach for valve exchange. In this type of approach, locating tool 230, holding tool 280, and valve removal tool 120A are inserted through an incision in the ascending aorta of the heart and advanced towards the aortic valve against the flow of blood. In the case of a mitral valve, valve member 20 can be exchanged using the tools 230, 280 and 120A in accordance with the previously disclosed "transapical" approach. It should be understood that to exchange a valve member 20 mounted in the mitral position, tools 230, 280 and 120A are passed through the apex of the heart either directly, or through a short trocar.

It should be appreciated that use of locating tool 230 may be unnecessary, since a physician with sufficient skill may be able to directly manipulate holding tool 280 into engagement with base member 40. Thus, it is contemplated that holding tool 280 may be engaged with base member 40 without the use of locating tool 230.

In summary, the retrograde approach to valve exchange includes the following sequence of steps:

(i) exposure of the ascending aorta of the heart and the establishment of a purse-string suture through which tools 230, 280 and 120A are inserted (it should be appreciated that a "trocar" can also be inserted through the same slit in the ascending aorta);

(ii) insertion of locating tool 230;

(iii) capture of valve assembly 10 with snare loops 254 of locating tool 230;

(iii) insertion of valve holding tool 280 and engagement with base member 40 of valve assembly 10;

(iv) removal of locating tool 230;

(v) insertion of valve removal tool 120A and grasping of coupling elements 30 of valve member 20;

(vi) dilation, unseating and collapse of valve member 20;

(vii) removal of valve member 20;

(viii) insertion of new valve member 20 using removal tool 120A as an installation tool (or a dedicated valve insertion tool);

(ix) expansion and seating of the new valve member 20 in base member 40;

(x) collapse and removal of removal tool 120A or the valve insertion tool;

(xi) collapse and removal of valve holding tool 280;

(xii) closure of the incision in the ascending aorta.

Figure 22:
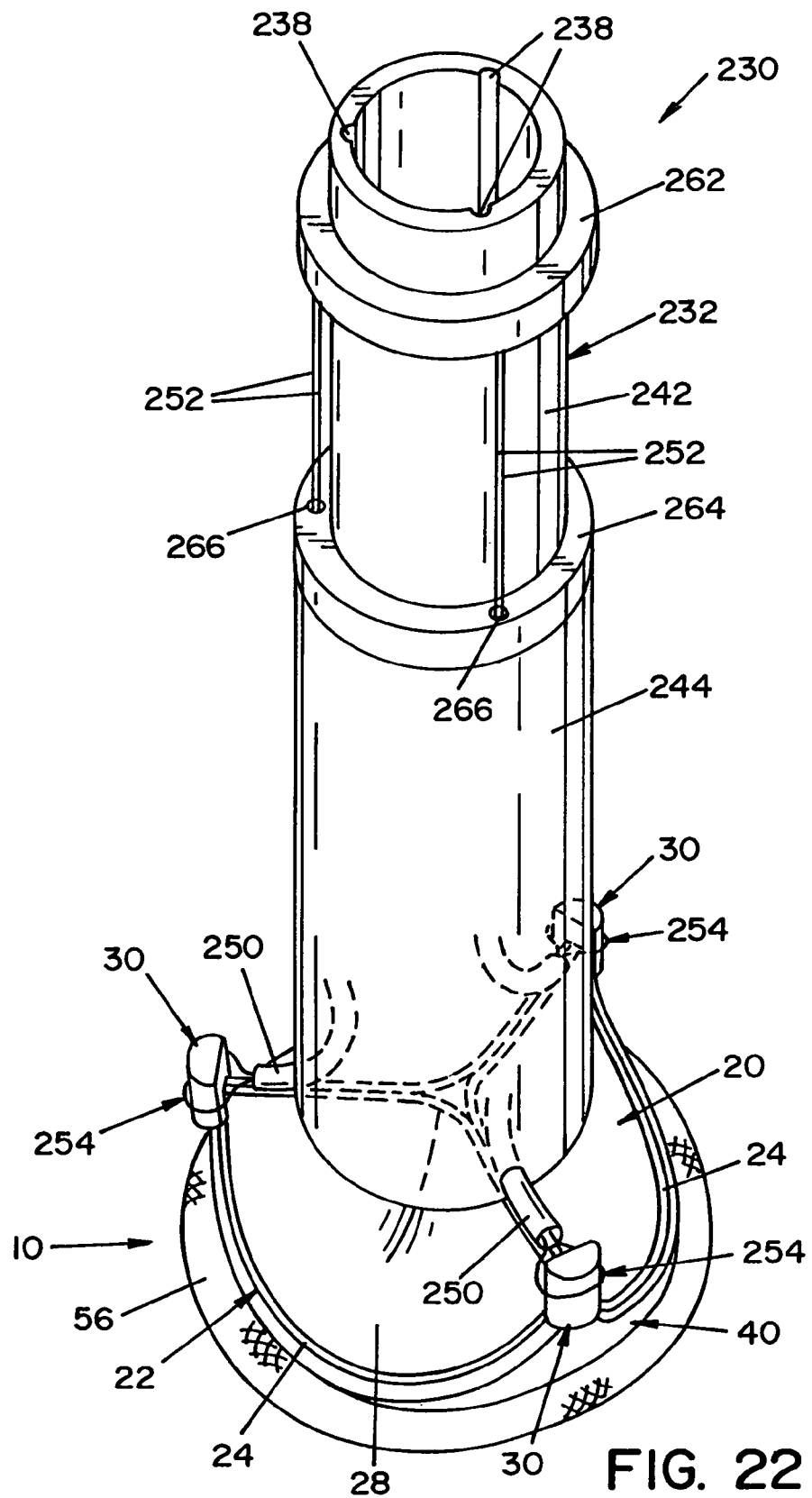
FIG. 22 is a perspective view of the locating tool of FIG. 17 showing tightened snare wires in engagement with the valve assembly.
Figure 26:
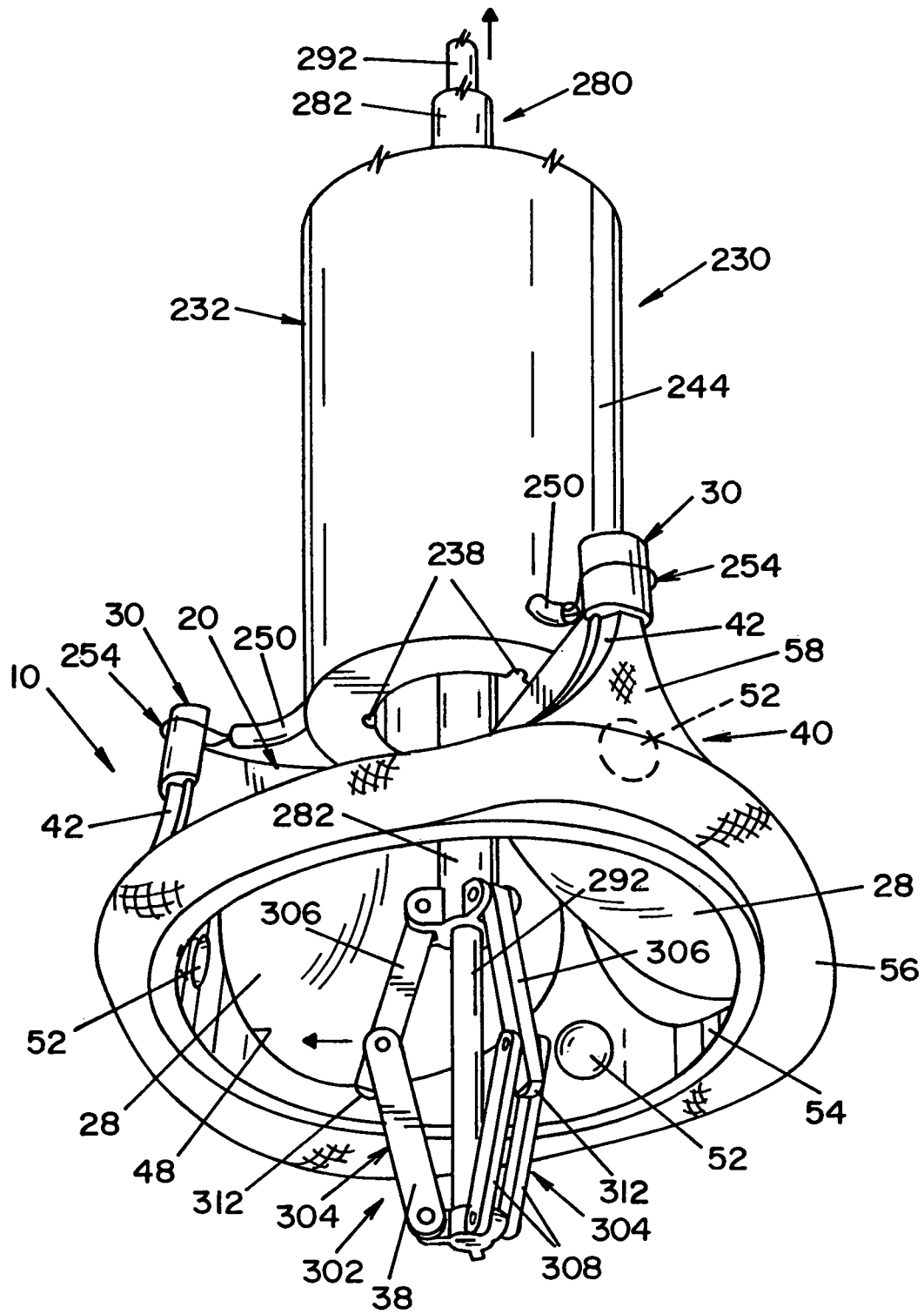
FIG. 26 shows holding tool of FIG. 23 inserted into the locating tool as shown in FIG. 22, wherein the holding tool is in a collapsed position.
Figure 27:
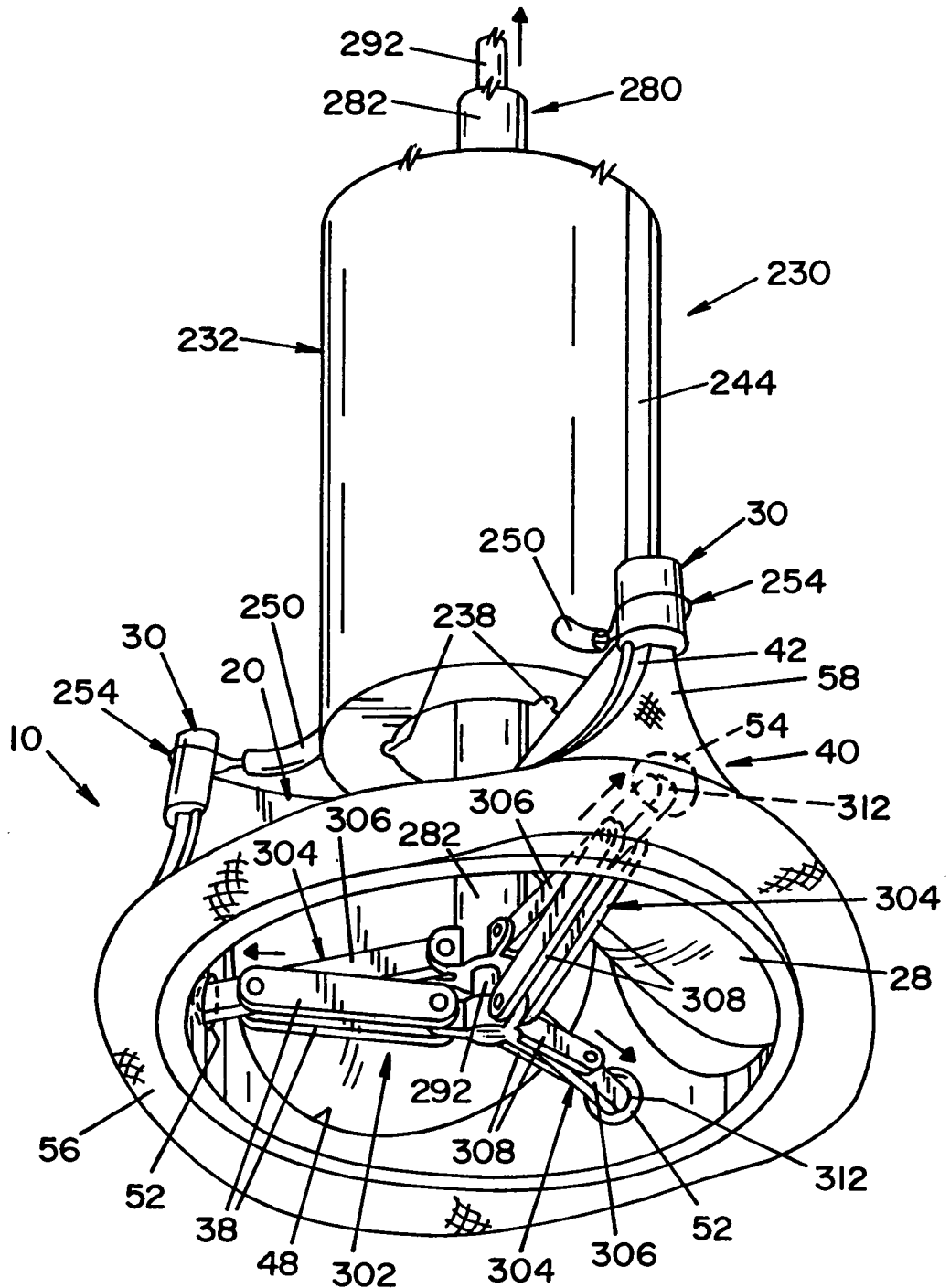
FIG. 27 shows holding tool of FIG. 23 inserted into the locating tool as shown in FIG. 22, wherein the holding tool is in an expanded position, thereby engaging with the base member of the valve assembly.

A valve removal procedure will now be described in detail with reference to FIGS. 26-29. Locating tool 230 is passed through a purse string incision in the ascending aorta and activated using moving rings 262 and 264 to engage with valve assembly 10, as shown in FIG. 22. Thereafter, holding tool 280 is inserted into tubular body 232 of locating tool 230 with articulating joint member 302 in the collapsed position, as shown in FIG. 26. Grooves 238 and locating means 288 are used to locate (i.e., pre-align) protuberances 312 of articulating joint member 302 in an appropriate position relative to depressions 52 of base member 40. Inner rod 292 is then moved relative to tubular body 282 to move articulating joint member 302 to the expanded position, thereby engaging holding tool 280 with base member 40, as seen in FIG. 27. Next, locating tool 230 is removed by disengaging snare loops 254 from valve assembly 10. In this regard, second moveable ring 264 is moved away from second section 244, thereby retracting sleeves 250. Furthermore, first moveable ring 262 is moved toward second section 244 to loosen snare loops 254.

Next, valve removal tool 120A is located in an appropriate position relative to coupling elements 30 of valve member 20 (FIG. 28). In this respect, grooves 208 of removal tool 120A and locating means 288 of holding tool 280 facilitate alignment of removal tool 120A relative to coupling elements 30. Valve removal tool 120A is then operated in the same manner as removal tool 120 to grasp coupling elements 30 and disengage valve member 20 from base member 40 (FIG. 29).

Tubular body 282 of holding tool 280 preferably has markings formed thereon so that the depth of insertion of removal tool 120A can be visualized and preset to correspond with the location of coupling elements 30 of valve member 20. In this manner, removal tool 120A can be easily and accurately passed over holding tool 280 to a prescribed depth without direct visualization.

It is contemplated that removal tool 120A, as disclosed herein or with minor modifications, may also function as a valve installation tool. In this regard, a valve member 20 may be inserted into a heart and engaged with base member 40 by reversing the steps of the operation discussed above for removal of valve member 20 from base member 40.

Figure 30:
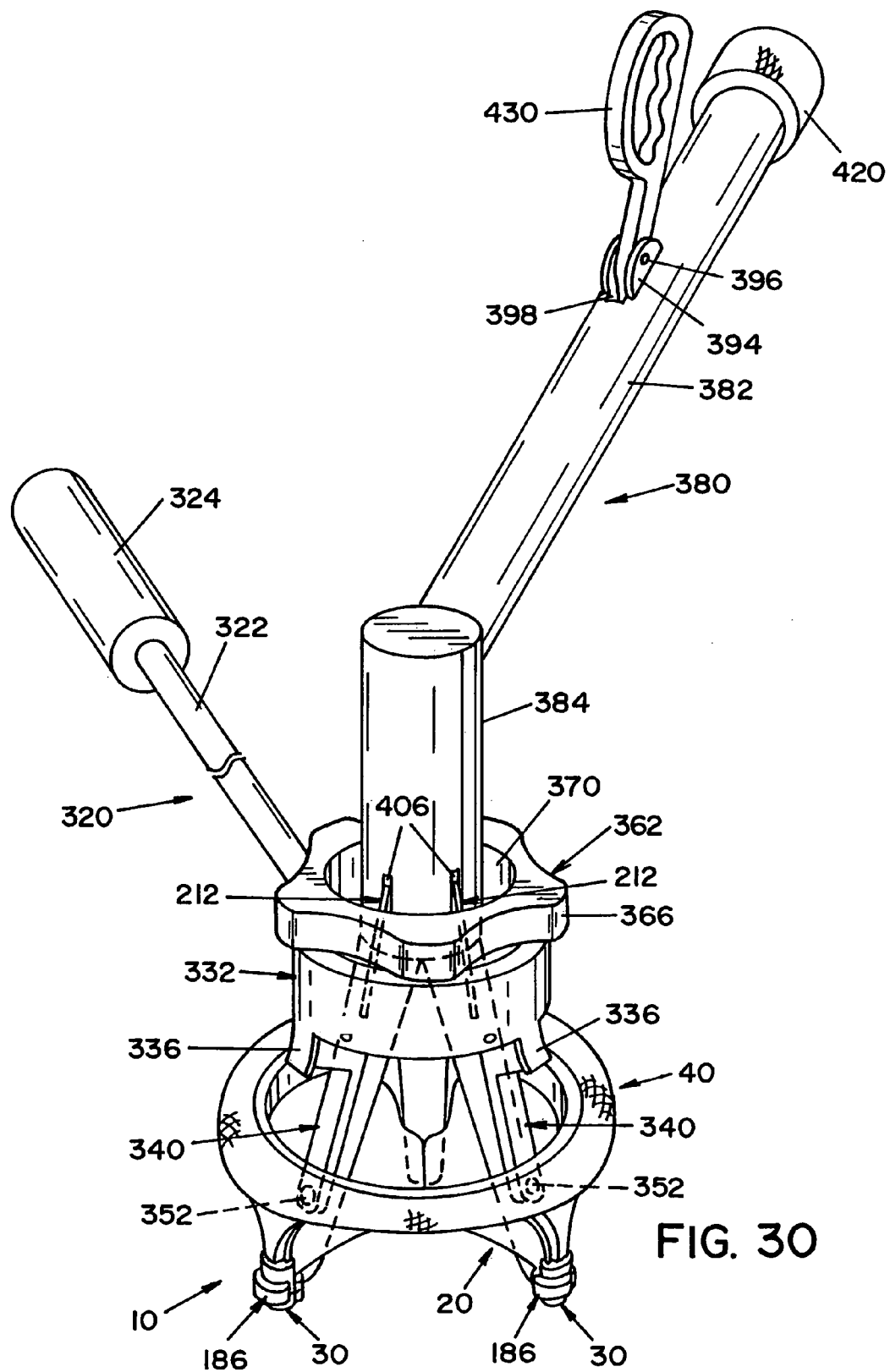
FIG. 30 is a perspective view of another embodiment of the valve holding tool and another embodiment of the valve removal tool, wherein the valve holding tool and valve removal tool are engaged with the valve assembly.
Figure 31A:
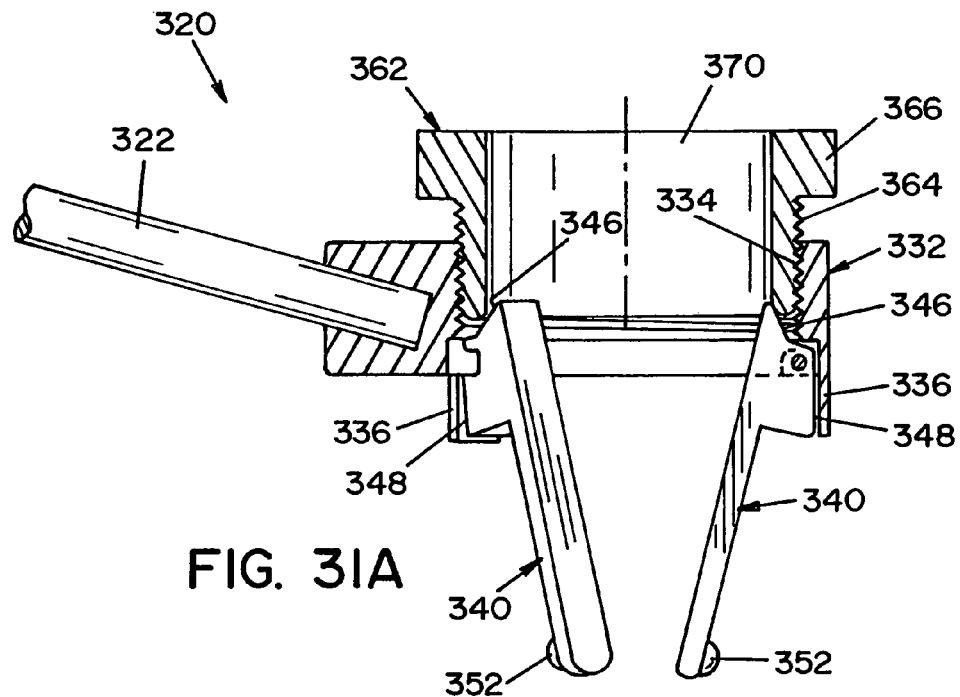
FIG. 31A is a cross-sectional view of the holding tool shown in FIG. 30, wherein the fingers of the holding tool are in a collapsed position.
Figure 31B:
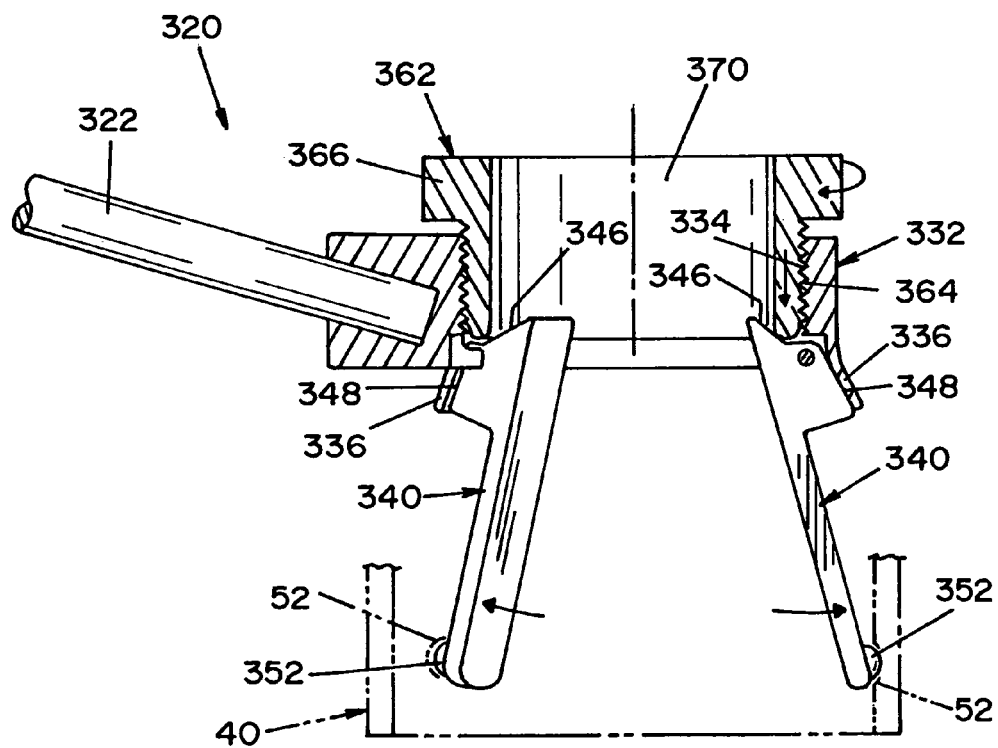
FIG. 31B is a cross-sectional view of the holding tool shown in FIG. 30, wherein the fingers of the holding tool are in an expanded position for engagement with the base member of the valve assembly.

Still further embodiments of a valve holding tool 320 and a valve removal tool 380 are shown in FIGS. 30, 31A, 31B and 32. With reference to FIGS. 30, 31A and 31B, holding tool 320 will now be described in detail. Holding tool 320 is generally comprised of a tubular body portion 332, a plurality of moveable fingers 340, a rotational actuator 362 and an elongated handle 322.

Body portion 332 includes inner threads 334 (FIGS. 31A and 31B) and downward extending flexible tabs 336. As best seen in FIGS. 31A and 31B, fingers 340 are pivotally connected with body portion 332. Fingers 340 include a first face 346 having a sloped surface and an outward facing second face 348 that is engageable with tabs 336. An outward facing protuberance 352 is formed at one end of finger 340, and is dimensioned to be received by depression 52 of base member 40, as shown in FIG. 31B.

For minimally invasive or "key-hole" surgery, it should be understood that tubular body portion 332 of valve holding tool 320 may be more elongated than as shown in the illustrated embodiment. Handle 322 is attached to body portion 332, and includes a gripping portion 324.

Actuator 362 is ring-shaped and includes outer thread 364 dimensioned to mate with inner threads 334 of body portion 332. Actuator 362 also includes a gripping member 366 formed of outward extending flanges.

Fingers 340 are moveable between a collapsed position (FIG. 31A) and an expanded position (FIG. 31B) by rotation of actuator 362. In this regard, as actuator 362 is rotated into body portion 332 it engages with first face 346 of fingers 340, thereby forcing fingers 340 to pivot outward. Second face 348 of fingers 340 engages with flexible tabs 336. Tabs 336 are preferably formed of a material having an elasticity such that tabs 336 return to their original position after being deformed by fingers 340.

Holding tool 320 provides a cylindrical recess 370 dimensioned to receive removal tool 380. Removal tool 380 is similar in many respects to removal tool 120 described in detail above, and will now be described with reference to FIGS. 30 and 32, wherein components of removal tool 380 similar to components of removal tool 120 bear the same reference numbers. Removal tool 380 is generally comprised of a first cylindrical body portion 382, a second cylindrical body portion 384, a gripping elements actuator 420, an arms actuator 430, a plurality of arms 180, a cylindrical inner sleeve 462 and a plurality of links 212. Arms 180 are described above, and include gripping elements 186. Links 212, having first and second ends 214, 216, are also described above. Slots 406 are formed in body portion 384 to receive first end 214 of links 212.

In the illustrated embodiment, body portions 382 and 384 are oriented relative to each other at an angle of approximately 30-45 degrees. Notches 386 and outer threads 388 are formed at one end of first cylindrical body portion 382. An inner bore 390 is formed in second cylindrical body portion 384. Bore 390 is dimensioned to receive cylindrical inner sleeve 462, described below.

Figure 32:
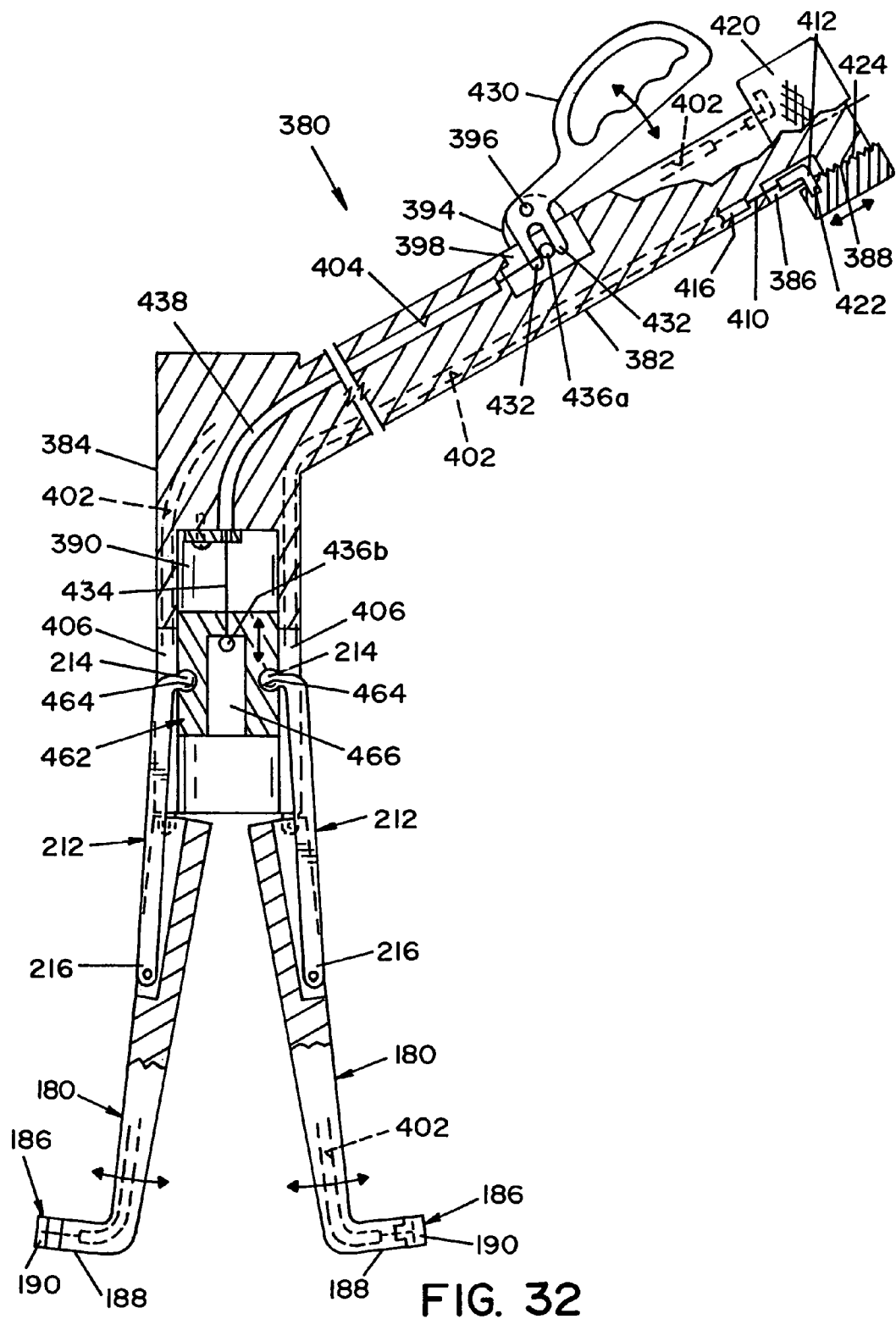
FIG. 32 is a cross-sectional view of the valve removal tool shown in FIG. 30.

A plurality of inner channels 402 extend through body portions 382, 384 and arms 180, as shown in FIG. 32. Each inner channel 402 is dimensioned to receive a cable 410 moveable within a sheath 416. The first end of each cable 410 has an L-shaped tab 412, while the second end of each cable 410 is connected with a gripping element 186 in the same manner as described above in connection with cable 150. A portion of L-shaped tabs 412 extend through notches 386 of body portion 382.

A channel 404 extends through body portions 382 and 384. Channel 404 is dimensioned to receive a cable 434 moveable within a sheath 438. The first end of cable 434 has a pin 436a, while the second end of cable 434 has a pin 436b.

A bracket member 394 extends outward from the outer surface of body portion 382. Bracket member 394 supports arms actuator 430 that is pivotally attached to bracket member 394 by a pivot pin 396. In the illustrated embodiment, actuator 430 is a "scissor-like" handle. Arms actuator 430 includes fingers 432 that extend through a slot 398 formed in body portion 382, as shown in FIG. 32. Fingers 432 capture pin 436a of cable 434.

Inner sleeve 462 is dimensioned to be received within bore 390 of body portion 384. Outward facing cavities 464 are formed in sleeve 462 to receive first end 214 of links 212. Sleeve 462 also includes an inner cavity 466. Pin 436b of cable 434 is captured within cavity 466. Rotation of actuator 430 causes movement of cable 434, thereby moving inner sleeve 462, which in turn moves arms 440 between the collapsed position and expanded position. Retraction of cable 434 causes inner sleeve 462 to move further into bore 390, thereby causing links 212 to move arms 180 outward to an expanded position.

In the illustrated embodiment, gripping elements actuator 420 takes the form of a cap screw having inner threads 424 that mate with outer threads 388 of body section 382, and an annular inner groove 422. Inner groove 422 is dimensioned to receive a portion of L-shaped tab 412 of cable 410. Rotation of actuator 420 results in movement of cable 410, thereby actuating gripping elements 186 in the same manner as described above in connection with removal tool 120.

FIG. 30 shows valve holding tool 320 engaged with base member 40, and valve removal tool 380 inserted through valve holding tool 320 in engagement with valve member 20. Valve assembly 10 is shown implanted in the mitral position.

It is contemplated that removal tool 380, as disclosed herein or with minor modifications, may also function as a valve installation tool. In this regard, a valve member 20 may be inserted into a heart and engaged with base member 40 by reversing the steps of the operation discussed below for removal of valve member 20 from base member 40.

An open surgical approach to valve exchange may involve the following sequence of steps:

(i) exposure of the heart through an incision into the chest;
(ii) cannulation of the various great vessels and establishment of cardiopulmonary bypass;
(iii) arresting of the heart through the infusion of cardioplegia into the coronary arteries;
(iv) exposure of the existing valve assembly 10 by an incision through the aorta (in the case of an aortic valve exchange) or though the left atrium (in the case of a mitral valve exchange);
(v) insertion of valve holding tool 320 and engagement with base member 40, as shown in FIG. 31B.
(vi) insertion of valve removal tool 380 through cylindrical recess 370 of holding tool 320, and grasping of the coupling elements of valve member 20;
(vii) dilation, unseating and collapse of valve member 20;
(viii) removal of valve member 20;
(ix) insertion of a new valve member 20 using valve removal tool 380 (or a dedicated valve insertion tool);
(x) expansion and seating of the new valve member in base member 40.
(xi) collapse and removal of valve removal tool 380 (or the dedicated valve insertion tool);
(xii) collapse and removal of valve holding tool 320;
(xiii) closure of the incision in the aorta or the left atrium; and
(xiv) establishment of normal heart function and removal of canulas.

The foregoing description is a specific embodiment of the present invention. It should be appreciated that this embodiment is described for purposes of illustration only, and that numerous alterations and modifications may be practiced by those skilled in the art without departing from the spirit and scope of the invention. It is intended that all such modifications and alterations be included insofar as they come within the scope of the invention.

Having described the invention, the following is claimed:

1. A set of tools for facilitating installation and removal of a valve member of the valve assembly that includes the valve member detachably coupled to a base member, the set of tools comprising:
   (a) a holding tool for holding the base member comprising:
      a first body;
      a plurality of fingers mounted to the first body and moveable between a collapsed position and an expanded position, said fingers engageable with the base member in the expanded position, and
      a finger actuator for actuating movement of the fingers between the collapsed and expanded positions; and
   (b) an exchange tool for installation and removal of a valve member, said exchange tool comprising:
      a second body,
      a plurality of arms mounted to the second body and moveable between a collapsed position and an expanded position, said arms engageable with the valve member in the expanded position, and
      a first actuator for actuating movement of the arms between the collapsed and expanded positions,.
   wherein one of said first body or said second body includes a groove and one of said first body or said second body includes a locating member, said groove dimensioned to engage with said locating member for limiting rotational axial movement of the exchange tool relative to the holding tool to orient the exchange tool relative to the valve member.

2. A set of tools according to claim 1, wherein each of said fingers of said holding tool includes a protuberance dimensioned to be received by a depression formed in a surface of said base member.

3. A set of tools according to claim 1, wherein each of said fingers of said holding tool includes a protuberance dimensioned to be received by a hole formed in said base member.

4. A set of tools according to claim 1, wherein each of said fingers of said holding tool includes a depression dimensioned to receive a protuberance formed in a surface of said base member.

5. A set of tools according to claim 1, wherein said first body defines a recess dimensioned to receive said exchange tool for detaching the valve member from the base member, and wherein said first body includes said groove and said second body includes said locating member.

6. A set of tools according to claim 5, wherein said recess has an inner surface that includes said groove.

7. A set of tools according to claim 1, wherein said holding tool further comprises:
   a plurality of rods connecting said actuator with said plurality of fingers.

8. A set of tools according to claim 1, wherein said plurality of fingers of said holding tool are pivotally connected with said first body.

9. A set of tools according to claim 1, wherein said finger actuator of said holding tool is rotatable to effect movement of said plurality of fingers.

10. A set of tools according to claim 1, wherein said second body includes said groove and said first body includes said locating member, wherein the groove of said exchange tool is dimensioned to engage with the locating member of said holding tool.

11. A set of tools according to claim 1, wherein each of said plurality of arms of said exchange tool includes a gripping element for grasping a portion of said valve member, said gripping element moveable between an open position and a closed position.

12. A set of tools according to claim 11, wherein said exchange tool further comprises:
a second actuator for actuating movement of the gripping elements between the open and closed positions.

13. A set of tools according to claim 11, wherein said second actuator moves a cable to effect movement of said gripping elements.

14. A set of tools according to claim 1, wherein said first actuator moves an inner sleeve relative to said second body in order to effect movement of said arms.

15. A set of tools according to claim 14, wherein said first actuator is connected with the inner sleeve by a cable.

16. A set of tools for facilitating the installation and removal of a valve member of a valve assembly that includes the valve member detachably coupled to a base member, the set of tools comprising:
(a) a holding tool for holding the base member comprising:
a tubular first body;
an inner rod moveable within the tubular first body;
an articulating joint member connected to the tubular first body and the inner rod, said articulating joint member moveable between a collapsed position and an expanded position, wherein movement of the inner rod relative to the tubular first body moves the articulating joint member between the collapsed and expanded positions; and
(b) an exchange tool for installation and removal of a valve member, said exchange tool comprising:
a second body,
a plurality of arms mounted to the second body and moveable between a collapsed position and an expanded position, said arms engageable with the valve member in the expanded position, and
a first actuator for actuating movement of the arms between the collapsed and expanded positions,
wherein one of said first body or said second body includes a groove and one of said first body or said second body includes a locating member, said groove dimensioned to engage with said locating member for limiting rotational axial movement of the exchange tool relative to the holding tool to orient the exchange tool relative to the valve member.

17. A set of tools according to claim 16, wherein said second body defines an opening dimensioned to receive said holding tool, and wherein said second body includes said groove and said first body includes said locating member.

18. A set of tools according to claim 17, wherein said groove is located within said opening.

19. A set of tools according to claim 16, wherein said articulating joint member is comprised of:
a plurality of articulating legs, each of said legs including a protuberance dimensioned to be received by a depression formed in the base member of the valve assembly.

20. A set of tools according to claim 19, wherein said articulating legs articulate such that said protuberances are maintained in alignment at a fixed angle relative to said depressions, as said legs are articulated.

21. A set of tools according to claim 16, wherein said first body includes the locating member.

22. A set of tools according to claim 16, wherein the set of tools further comprises:
a locating tool comprising:
a third body defining an opening dimensioned to receive the holding tool engageable with said base member,
a plurality of snare loops, each snare loop comprised of a snare wire,
a plurality of moveable sleeves, each sleeve enclosing a portion of a snare wire,
first control means for moving the snare loops between a retracted position and a loosened position, and
second control means for moving the sleeves between a retracted position and an extended position.

23. A set of tools according to claim 22, wherein said first control means of said locating tool is a first sliding ring connected with the snare wires.

24. A set of tools according to claim 22, wherein said second control means of said locating tool is a second sliding ring connected with the sleeves.

25. A set of tools according to claim 22, wherein said snare loops are connected to adjacent snare loops by an adhesive.

* * * * *